(12) United States Patent
Lipkens et al.

(10) Patent No.: US 10,975,368 B2
(45) Date of Patent: Apr. 13, 2021

(54) ACOUSTOPHORESIS DEVICE WITH DUAL ACOUSTOPHORETIC CHAMBER

(71) Applicant: FloDesign Sonics, Inc., Wilbraham, MA (US)

(72) Inventors: Bart Lipkens, Hampden, MA (US); Brian McCarthy, Ludlow, MA (US); Ben Ross-Johnsrud, Wilbraham, MA (US); Jason Barnes, Westfield, MA (US); Dane Mealey, Somers, CT (US); Thomas J. Kennedy, III, Wilbraham, MA (US)

(73) Assignee: FloDesign Sonics, Inc., Wilbraham, MA (US)

(*) Notice: Subject to any disclaimer, the term of this patent is extended or adjusted under 35 U.S.C. 154(b) by 351 days.

(21) Appl. No.: 15/672,288

(22) Filed: Aug. 8, 2017

(65) Prior Publication Data
US 2017/0369865 A1 Dec. 28, 2017

Related U.S. Application Data

(62) Division of application No. 14/592,337, filed on Jan. 8, 2015, now Pat. No. 9,725,710.

(60) Provisional application No. 61/925,171, filed on Jan. 8, 2014.

(51) Int. Cl.
- *C12N 13/00* (2006.01)
- *B01D 21/28* (2006.01)

(52) U.S. Cl.
CPC ........... *C12N 13/00* (2013.01); *B01D 21/283* (2013.01)

(58) Field of Classification Search
None
See application file for complete search history.

(56) References Cited

U.S. PATENT DOCUMENTS

| | | | |
|---|---|---|---|
| 2,473,971 A | 6/1949 | Ross |
| 2,667,944 A | 2/1954 | Crites |
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,125,789 A | 11/1978 | Van Schoiack |
| 4,158,629 A | 6/1979 | Sawyer |
| 4,165,273 A | 8/1979 | Azarov et al. |
| 4,173,725 A | 11/1979 | Asai et al. |

(Continued)

FOREIGN PATENT DOCUMENTS

| | | |
|---|---|---|
| AU | 2002236405 | 9/2002 |
| CN | 105 087 788 A | 11/2015 |

(Continued)

OTHER PUBLICATIONS

Alvarez et al.; Shock Waves, vol. 17, No. 6, pp. 441-447, 2008.

(Continued)

*Primary Examiner* — Ryan B Huang
(74) *Attorney, Agent, or Firm* — FloDesign Sonics, Inc.

(57) ABSTRACT

An acoustophoresis device includes an acoustic chamber with a piezoelectric element located within its volume. The piezoelectric element vibrates and generates acoustic standing waves from both sides, so that particles can be separated from fluid passing through the acoustic chamber. This permits the element to be cooled more efficiently, reducing transient heat loads in the fluid traveling through the device.

11 Claims, 10 Drawing Sheets

(56) References Cited

U.S. PATENT DOCUMENTS

| | | |
|---|---|---|
| 4,204,096 A | 5/1980 | Barcus et al. |
| 4,211,949 A | 7/1980 | Brisken |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,484,907 A | 11/1984 | Sheeran, Jr. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,562,823 A | 10/1996 | Reeves |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,844,140 A | 12/1998 | Seale |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,029,518 A | 2/2000 | Oeftering |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,674,630 B2 | 3/2010 | Siversson |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,865,003 B2 | 10/2014 | Yang |
| 8,873,051 B2 | 10/2014 | Kaduchak et al. |
| 8,889,388 B2 | 11/2014 | Wang et al. |
| 9,023,658 B2 | 5/2015 | Gauer et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,375,662 B2 | 6/2016 | Kambayashi et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,605,074 B2 | 3/2017 | Shah |
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |

(56) References Cited

U.S. PATENT DOCUMENTS

| | | |
|---|---|---|
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 | 6/2017 | Lipkens et al. |
| 9,670,938 B2 | 6/2017 | Beliaysky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 9,810,665 B2 | 11/2017 | Fernald et al. |
| 9,833,763 B2 | 12/2017 | Fernald et al. |
| 9,869,618 B2 | 1/2018 | Hoyos |
| 9,869,659 B2 | 1/2018 | Buckland et al. |
| 9,872,900 B2 | 1/2018 | Ciaramella et al. |
| 9,873,126 B2 | 1/2018 | Mao et al. |
| 9,873,894 B2 | 1/2018 | Conway et al. |
| 9,878,056 B2 | 1/2018 | Bancel et al. |
| 9,878,536 B2 | 1/2018 | Foresti et al. |
| 9,879,087 B2 | 1/2018 | DeSander et al. |
| 9,902,974 B2 | 1/2018 | Conway et al. |
| 9,907,846 B2 | 3/2018 | Morein et al. |
| 9,908,288 B2 | 3/2018 | Harkness |
| 9,909,117 B2 | 3/2018 | Kaduchak |
| 9,909,313 B1 | 3/2018 | Grubbs |
| 9,913,656 B2 | 3/2018 | Stulen |
| 9,913,866 B2 | 3/2018 | O'Shea et al. |
| 9,925,277 B2 | 3/2018 | Almarsson et al. |
| 9,926,382 B2 | 3/2018 | Fischer et al. |
| 9,937,207 B2 | 4/2018 | Gregory et al. |
| 9,938,390 B2 | 4/2018 | Storti et al. |
| 9,943,599 B2 | 4/2018 | Gehlt et al. |
| 9,944,702 B2 | 4/2018 | Galetto |
| 9,944,709 B2 | 4/2018 | Galetto |
| 9,994,743 B2 | 4/2018 | Ei-Zahab |
| 9,974,898 B2 | 5/2018 | Spain et al. |
| 9,983,459 B2 | 5/2018 | Arnold |
| 10,006,052 B2 | 6/2018 | Jarjour |
| 10,045,913 B2 | 8/2018 | Warner |
| 10,046,028 B2 | 8/2018 | Gregory |
| 10,046,037 B2 | 8/2018 | Weinschenk et al. |
| 10,047,116 B2 | 8/2018 | Morein |
| 10,047,123 B2 | 8/2018 | Weinschenk et al. |
| 10,047,124 B2 | 8/2018 | Weinschenk et al. |
| 10,047,144 B2 | 8/2018 | Elson et al. |
| 10,047,365 B2 | 8/2018 | Williams |
| 10,047,451 B2 | 8/2018 | Gaben |
| 10,047,650 B2 | 8/2018 | Abram |
| 10,052,427 B2 | 8/2018 | Flieg |
| 10,052,431 B2 | 8/2018 | Dreschel |
| 10,052,631 B2 | 8/2018 | Ben-Yakar et al. |
| 10,071,148 B2 | 9/2018 | Weinschenk |
| 10,071,383 B2 | 9/2018 | Dionne |
| 10,072,062 B2 | 9/2018 | Collingwood |
| 10,073,098 B2 | 9/2018 | Wong |
| 10,076,574 B2 | 9/2018 | Wang |
| 10,160,786 B1 | 12/2018 | Weinschenk et al. |
| 10,166,255 B2 | 1/2019 | Moriarity et al. |
| 10,166,323 B2 | 1/2019 | Fiering et al. |
| 10,167,317 B1 | 1/2019 | Stickel et al. |
| 10,167,474 B2 | 1/2019 | Rossi et al. |
| 10,167,478 B2 | 1/2019 | Williams |
| 10,175,249 B2 | 1/2019 | Lavinder et al. |
| 10,190,113 B2 | 1/2019 | Forsyth |
| 10,190,137 B2 | 1/2019 | Zhang et al. |
| 10,195,605 B2 | 2/2019 | Reinbigler |
| 10,196,608 B2 | 2/2019 | Poirot |
| 10,196,651 B2 | 2/2019 | Conway et al. |
| 10,196,652 B2 | 2/2019 | Conway et al. |
| 10,201,365 B2 | 2/2019 | Boudreaux et al. |
| 10,201,652 B2 | 2/2019 | Dutra et al. |
| 10,202,457 B2 | 2/2019 | Ruiz-Opazo et al. |
| 10,202,762 B2 | 2/2019 | Sollohub |
| 10,208,300 B2 | 2/2019 | Messina et al. |
| 10,214,013 B2 | 2/2019 | Foresti et al. |
| 10,214,718 B2 | 2/2019 | Berteau et al. |
| 10,215,760 B2 | 2/2019 | Grove |
| 10,221,843 B2 | 3/2019 | Locker |
| 10,224,015 B2 | 3/2019 | Hsu |
| 10,236,797 B2 | 3/2019 | Wischnewskiy |
| 10,238,365 B2 | 3/2019 | Shiraishi |
| 10,238,741 B2 | 3/2019 | Creusot |
| 10,239,058 B2 | 3/2019 | Lavieu et al. |
| 10,239,948 B2 | 3/2019 | Jullerat et al. |
| 10,245,064 B2 | 4/2019 | Rhee et al. |
| 10,251,664 B2 | 4/2019 | Shelton et al. |
| 10,253,296 B2 | 4/2019 | Kahvejian et al. |
| 10,254,212 B2 | 4/2019 | Ward |
| 10,254,401 B2 | 4/2019 | Suyama |
| 10,258,698 B2 | 4/2019 | Hoge et al. |
| 10,261,078 B2 | 4/2019 | Branch |
| 10,272,163 B2 | 4/2019 | Laterza |
| 10,272,412 B2 | 4/2019 | Rubio Martinez et al. |
| 10,273,283 B2 | 4/2019 | Springer et al. |
| 10,286,007 B2 | 5/2019 | Galetto et al. |
| 10,308,928 B2 | 6/2019 | Lipkens et al. |
| 10,316,063 B1 | 6/2019 | Weinschenk et al. |
| 10,316,101 B2 | 6/2019 | Galetto et al. |
| 10,322,949 B2 | 6/2019 | Lipkens et al. |
| 10,323,065 B1 | 6/2019 | Weinschenk et al. |
| 10,323,076 B2 | 6/2019 | Ellsworth et al. |
| 10,324,082 B2 | 6/2019 | Taylor et al. |
| 10,326,383 B2 | 6/2019 | Stiebel et al. |
| 10,329,531 B2 | 6/2019 | Kahvejian et al. |
| 10,334,390 B2 | 6/2019 | Bakish |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0057886 A1 | 3/2004 | Jona Zumeris et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0055136 A1 | 3/2005 | Hoffman |
| 2005/0121269 A1 | 6/2005 | Namduri |
| 2005/0145567 A1 | 7/2005 | Quintel et al. |
| 2005/0196725 A1 | 9/2005 | Fu |
| 2005/0239198 A1 | 10/2005 | Kunas |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0138108 A1 | 6/2007 | Hadfield et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |

(56) References Cited

U.S. PATENT DOCUMENTS

| | | |
|---|---|---|
| 2009/0042253 A1 | 2/2009 | Hiller et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0207225 A1 | 8/2011 | Mehta et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0161903 A1 | 6/2012 | Thomas et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0206688 A1 | 8/2013 | El-Naas |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2013/0309757 A1 | 11/2013 | Kim |
| 2014/0011240 A1 | 1/2014 | Lipkens et al. |
| 2014/0017758 A1 | 1/2014 | Kniep et al. |
| 2014/0033808 A1 | 2/2014 | Ding et al. |
| 2014/0102947 A1 | 4/2014 | Baym et al. |
| 2014/0141413 A1 | 5/2014 | Laugham, Jr. et al. |
| 2014/0154795 A1 | 6/2014 | Lipkens et al. |
| 2014/0230912 A1 | 8/2014 | Aider et al. |
| 2014/0319077 A1 | 10/2014 | Lipkens et al. |
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0252317 A1 | 9/2015 | Lipkens et al. |
| 2015/0274550 A1 | 10/2015 | Lipkens et al. |
| 2015/0321129 A1 | 11/2015 | Lipkens et al. |
| 2016/0060615 A1 | 3/2016 | Walther et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0287778 A1 | 10/2016 | Leach et al. |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III et al. |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao et al. |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0080423 A1 | 3/2017 | Dauson et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarty et al. |
| 2017/0128523 A1 | 5/2017 | Ghatnekar et al. |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |

(56) References Cited

U.S. PATENT DOCUMENTS

| | | |
|---|---|---|
| 2017/0145094 A1 | 5/2017 | Galetto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper et al. |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0189450 A1 | 7/2017 | Conway et al. |
| 2017/0190767 A1 | 7/2017 | Schurpf et al. |
| 2017/0191022 A1 | 7/2017 | Lipkens et al. |
| 2017/0232439 A1 | 8/2017 | Suresh et al. |
| 2017/0374730 A1 | 12/2017 | Flores |
| 2018/0000311 A1 | 1/2018 | Lipkens et al. |
| 2018/0000870 A1 | 1/2018 | Britt |
| 2018/0000910 A1 | 1/2018 | Chakraborty et al. |
| 2018/0001011 A1 | 1/2018 | Paschon et al. |
| 2018/0008707 A1 | 1/2018 | Bussmer et al. |
| 2018/0009158 A1 | 1/2018 | Harkness et al. |
| 2018/0009888 A9 | 1/2018 | Baumeister et al. |
| 2018/0009895 A1 | 1/2018 | Smith et al. |
| 2018/0010085 A1 | 1/2018 | Lipkens et al. |
| 2018/0014846 A1 | 1/2018 | Rhee |
| 2018/0015128 A1 | 1/2018 | Britt |
| 2018/0015392 A1 | 1/2018 | Lipkens et al. |
| 2018/0016570 A1 | 1/2018 | Lipkens et al. |
| 2018/0016572 A1 | 1/2018 | Tang |
| 2018/0020295 A1 | 1/2018 | Pander et al. |
| 2018/0021379 A1 | 1/2018 | Galetto et al. |
| 2018/0022798 A1 | 1/2018 | Shurpf et al. |
| 2018/0028683 A1 | 2/2018 | Wong et al. |
| 2018/0043473 A1 | 2/2018 | Helvajian et al. |
| 2018/0049767 A1 | 2/2018 | Gee et al. |
| 2018/0051089 A1 | 2/2018 | Galettto et al. |
| 2018/0051265 A1 | 2/2018 | Cooper |
| 2018/0052095 A1 | 2/2018 | Cumbo et al. |
| 2018/0052147 A1 | 2/2018 | Zeng |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0055997 A1 | 3/2018 | Cabrera et al. |
| 2018/0056095 A1 | 3/2018 | Messerly et al. |
| 2018/0057810 A1 | 3/2018 | Zhang et al. |
| 2018/0058439 A1 | 3/2018 | Locke et al. |
| 2018/0066223 A1 | 3/2018 | Lim |
| 2018/0066224 A1 | 3/2018 | Lipkens et al. |
| 2018/0066242 A1 | 3/2018 | Zhang |
| 2018/0067044 A1 | 3/2018 | Kaduchak et al. |
| 2018/0071363 A1 | 3/2018 | Ghatnekar et al. |
| 2018/0071981 A1 | 3/2018 | Collino et al. |
| 2018/0078268 A1 | 3/2018 | Messerly |
| 2018/0080026 A1 | 3/2018 | Rossi et al. |
| 2018/0085743 A1 | 3/2018 | Yavorsky et al. |
| 2018/0087044 A1 | 3/2018 | Lipkens et al. |
| 2018/0088083 A1 | 3/2018 | Sinha |
| 2018/0092338 A1 | 4/2018 | Hering et al. |
| 2018/0092660 A1 | 4/2018 | Ethicon |
| 2018/0094022 A1 | 4/2018 | Bracewell et al. |
| 2018/0095067 A1 | 4/2018 | Huff et al. |
| 2018/0098785 A1 | 4/2018 | Price et al. |
| 2018/0100134 A1 | 4/2018 | Lim |
| 2018/0100204 A1 | 4/2018 | O'Shea |
| 2018/0119174 A1 | 5/2018 | Scharenberg et al. |
| 2018/0130491 A1 | 5/2018 | Mathur |
| 2018/0136167 A1 | 5/2018 | Smith et al. |
| 2018/0140758 A1 | 5/2018 | Vincent et al. |
| 2018/0143138 A1 | 5/2018 | Shreve et al. |
| 2018/0143167 A1 | 5/2018 | Mziray et al. |
| 2018/0147245 A1 | 5/2018 | O'Shea et al. |
| 2018/0147576 A1 | 5/2018 | Lavieu et al. |
| 2018/0148740 A1 | 5/2018 | Conway et al. |
| 2018/0148763 A1 | 5/2018 | Shimada et al. |
| 2018/0153946 A1 | 6/2018 | Alemany et al. |
| 2018/0155716 A1 | 6/2018 | Zhang et al. |
| 2018/0157107 A1 | 6/2018 | Koyama |
| 2018/0161775 A1 | 6/2018 | Kapur et al. |
| 2018/0177490 A1 | 6/2018 | Shiraishi |
| 2018/0178184 A1 | 6/2018 | Holland |
| 2018/0180610 A1 | 6/2018 | Taha |
| 2018/0223256 A1 | 8/2018 | Kim |
| 2018/0223273 A1 | 8/2018 | Lipkens |
| 2018/0223439 A1 | 8/2018 | Lipkens |
| 2018/0230433 A1 | 8/2018 | Kokkaliaris |
| 2018/0231555 A1 | 8/2018 | Davis |
| 2018/0236103 A1 | 8/2018 | Friedland |
| 2018/0236280 A1 | 8/2018 | Lipkens et al. |
| 2018/0237533 A1 | 8/2018 | Juillerat et al. |
| 2018/0237768 A1 | 8/2018 | Reik |
| 2018/0237798 A1 | 8/2018 | Duchateau et al. |
| 2018/0243382 A1 | 8/2018 | Wang |
| 2018/0243665 A1 | 8/2018 | Lacki |
| 2018/0244722 A1 | 8/2018 | Stickel |
| 2018/0246103 A1 | 8/2018 | Lipkens |
| 2018/0249688 A1 | 9/2018 | Ayares |
| 2018/0250424 A1 | 9/2018 | Cotta-Ramusino |
| 2018/0251723 A1 | 9/2018 | Murthy |
| 2018/0251770 A1 | 9/2018 | Friedland |
| 2018/0255751 A1 | 9/2018 | Regev |
| 2018/0256922 A1 | 9/2018 | Mittelstein |
| 2018/0257042 A1 | 9/2018 | Hester |
| 2018/0257076 A1 | 9/2018 | Weitz |
| 2018/0258160 A1 | 9/2018 | Lai |
| 2018/0258955 A1 | 9/2018 | Levasseur |
| 2018/0258957 A1 | 9/2018 | Levasseur |
| 2018/0296954 A1 | 10/2018 | Trampler |
| 2018/0353614 A1 | 12/2018 | Peters |
| 2018/0361053 A1 | 12/2018 | Fiering et al. |
| 2018/0361383 A1 | 12/2018 | Kapur et al. |
| 2018/0361384 A1 | 12/2018 | Kapur et al. |
| 2018/0369816 A1 | 12/2018 | Ai |
| 2018/0371418 A1 | 12/2018 | Yang et al. |
| 2019/0000932 A1 | 1/2019 | Martini |
| 2019/0000933 A1 | 1/2019 | Martini |
| 2019/0000947 A1 | 1/2019 | Weinschenk et al. |
| 2019/0000959 A1 | 1/2019 | Ciaramella et al. |
| 2019/0000982 A1 | 1/2019 | Wang et al. |
| 2019/0002497 A1 | 1/2019 | Stickel et al. |
| 2019/0002504 A1 | 1/2019 | Weinschenk et al. |
| 2019/0002561 A1 | 1/2019 | Galetto |
| 2019/0002573 A1 | 1/2019 | Galetto |
| 2019/0002578 A1 | 1/2019 | Brayshaw et al. |
| 2019/0002589 A1 | 1/2019 | Bardroff et al. |
| 2019/0002890 A1 | 1/2019 | Martini et al. |
| 2019/0004052 A1 | 1/2019 | Herd et al. |
| 2019/0008943 A1 | 1/2019 | Poolman et al. |
| 2019/0008948 A1 | 1/2019 | Ciaramella et al. |
| 2019/0010190 A1 | 1/2019 | Weinschenk et al. |
| 2019/0010192 A1 | 1/2019 | Binder et al. |
| 2019/0010471 A1 | 1/2019 | Zhang et al. |
| 2019/0010495 A1 | 1/2019 | Boitano et al. |
| 2019/0010514 A1 | 1/2019 | Poirot et al. |
| 2019/0011407 A9 | 1/2019 | Lipkens et al. |

(56) References Cited

U.S. PATENT DOCUMENTS

| | | |
|---|---|---|
| 2019/0015501 A1 | 1/2019 | Ciaramella et al. |
| 2019/0016753 A1 | 1/2019 | Jang et al. |
| 2019/0016767 A1 | 1/2019 | Shah |
| 2019/0016781 A1 | 1/2019 | Bolen |
| 2019/0022019 A1 | 1/2019 | Martini |
| 2019/0023577 A1 | 1/2019 | Feng |
| 2019/0024114 A1 | 1/2019 | Bauer |
| 2019/0030073 A1 | 1/2019 | Kalayoglu |
| 2019/0030151 A1 | 1/2019 | Jones et al. |
| 2019/0030533 A1 | 1/2019 | Shachar et al. |
| 2019/0031780 A1 | 1/2019 | Eavarone et al. |
| 2019/0031999 A1 | 1/2019 | Suresh et al. |
| 2019/0032036 A1 | 1/2019 | Zhang |
| 2019/0032052 A1 | 1/2019 | Zhang |
| 2019/0036152 A1 | 1/2019 | Gaben et al. |
| 2019/0036172 A1 | 1/2019 | Gaben et al. |
| 2019/0004806 A1 | 2/2019 | Smeland et al. |
| 2019/0006036 A1 | 2/2019 | Moriarty et al. |
| 2019/0038671 A1 | 2/2019 | Fan et al. |
| 2019/0039060 A1 | 2/2019 | Chien et al. |
| 2019/0040099 A1 | 2/2019 | Brellisford et al. |
| 2019/0040117 A1 | 2/2019 | Elson et al. |
| 2019/0040414 A1 | 2/2019 | Wu |
| 2019/0046986 A1 | 2/2019 | Yuan et al. |
| 2019/0048060 A1 | 2/2019 | Conway et al. |
| 2019/0054112 A1 | 2/2019 | Gregoire |
| 2019/0054119 A1 | 2/2019 | Alma et al. |
| 2019/0054122 A1 | 2/2019 | Moriarity et al. |
| 2019/0055286 A1 | 2/2019 | Walz et al. |
| 2019/0055509 A1 | 2/2019 | Meacham et al. |
| 2019/0056302 A1 | 2/2019 | Berezin et al. |
| 2019/0056399 A1 | 2/2019 | Wong et al. |
| 2019/0060363 A1 | 2/2019 | Moriarity et al. |
| 2019/0062185 A1 | 2/2019 | Amouzadeh et al. |
| 2019/0062690 A1 | 2/2019 | Tostoes et al. |
| 2019/0062735 A1 | 2/2019 | Welstead et al. |
| 2019/0064146 A1 | 2/2019 | Glick |
| 2019/0067554 A1 | 2/2019 | Karrai et al. |
| 2019/0070233 A1 | 3/2019 | Yeung |
| 2019/0070528 A1 | 3/2019 | Luthe |
| 2019/0071695 A1 | 3/2019 | Wagner |
| 2019/0071717 A1 | 3/2019 | Zhang et al. |
| 2019/0076473 A1 | 3/2019 | Nguyen |
| 2019/0076769 A1 | 3/2019 | Meacham et al. |
| 2019/0078133 A1 | 3/2019 | Cavanagh et al. |
| 2019/0079070 A1 | 3/2019 | Shiffman et al. |
| 2019/0083533 A1 | 3/2019 | Soon-Shiong et al. |
| 2019/0085067 A1 | 3/2019 | Schurpf et al. |
| 2019/0085082 A1 | 3/2019 | Bicknell |
| 2019/0085381 A1 | 3/2019 | Neely et al. |
| 2019/0090900 A1 | 3/2019 | Rhee et al. |
| 2019/0091683 A1 | 3/2019 | Baudoin et al. |
| 2019/0092794 A1 | 3/2019 | Rubio Martinez et al. |
| 2019/0092865 A1 | 3/2019 | Ruiz-Opazo |
| 2019/0093097 A1 | 3/2019 | Madison et al. |
| 2019/0094185 A1 | 3/2019 | Athanassiadis |
| 2019/0101541 A1 | 4/2019 | Wandall et al. |
| 2019/0105043 A1 | 4/2019 | Jaworek et al. |
| 2019/0106039 A1 | 4/2019 | Winton et al. |
| 2019/0106710 A1 | 4/2019 | Zhang et al. |
| 2019/0107420 A1 | 4/2019 | Kincel |
| 2019/0111480 A1 | 4/2019 | Barbati et al. |
| 2019/0119387 A1 | 4/2019 | Brett |
| 2019/0119701 A1 | 4/2019 | Liang et al. |
| 2019/0125839 A1 | 5/2019 | Frederick et al. |
| 2019/0127685 A1 | 5/2019 | Fattah et al. |
| 2019/0133633 A1 | 5/2019 | Neurohr et al. |
| 2019/0135942 A1 | 5/2019 | Duthe et al. |
| 2019/0136261 A1 | 5/2019 | Conway |
| 2019/0143013 A1 | 5/2019 | Vincent et al. |
| 2019/0153027 A1 | 5/2019 | Natarajan et al. |
| 2019/0153106 A1 | 5/2019 | Ruiz-Opazo et al. |
| 2019/0160463 A1 | 5/2019 | Ai et al. |
| 2019/0161540 A1 | 5/2019 | Gearing et al. |
| 2019/0167722 A1 | 6/2019 | Soon-Shiong et al. |
| 2019/0169233 A1 | 6/2019 | Weinschenk et al. |
| 2019/0169597 A1 | 6/2019 | Astrakhan et al. |
| 2019/0169639 A1 | 6/2019 | Zhang et al. |
| 2019/0170745 A1 | 6/2019 | Hu et al. |
| 2019/0173129 A1 | 6/2019 | Gaben et al. |
| 2019/0175517 A1 | 6/2019 | Martini et al. |
| 2019/0175651 A1 | 6/2019 | Lee et al. |
| 2019/0177368 A1 | 6/2019 | Weinschenk et al. |
| 2019/0177369 A1 | 6/2019 | Weinschenk et al. |
| 2019/0183931 A1 | 6/2019 | Alice et al. |
| 2019/0184035 A1 | 6/2019 | Jarjour et al. |
| 2019/0184312 A1 | 6/2019 | Liu et al. |
| 2019/0185860 A1 | 6/2019 | Kim et al. |
| 2019/0191252 A1 | 6/2019 | Lipkens et al. |
| 2019/0192653 A1 | 6/2019 | Hoge |
| 2019/0194049 A1 | 6/2019 | Lindemann |
| 2019/0194087 A1 | 6/2019 | Larsen |
| 2019/0194340 A1 | 6/2019 | Emtage et al. |
| 2019/0199312 A1 | 6/2019 | Dasgupta et al. |
| 2019/0199322 A1 | 6/2019 | Dasgupta et al. |

FOREIGN PATENT DOCUMENTS

| | | |
|---|---|---|
| CN | 104722106 B | 4/2016 |
| DE | 30 27 433 A1 | 2/1982 |
| DE | 32 18 488 A1 | 11/1983 |
| DE | 196 48 519 A1 | 6/1998 |
| DE | 103 19 467 B3 | 7/2004 |
| DE | 10 2008 006 501 A1 | 9/2008 |
| DE | 10 2014 206 823 A1 | 10/2015 |
| EP | 0 292 470 B1 | 11/1988 |
| EP | 0 167 406 B1 | 7/1991 |
| EP | 0 641 606 | 3/1995 |
| EP | 1 175 931 A1 | 1/2002 |
| EP | 1 254 669 B1 | 11/2002 |
| EP | 1 308 724 A2 | 5/2003 |
| EP | 2 209 545 | 7/2010 |
| EP | 270152 A1 | 1/2018 |
| EP | 2419511 | 1/2018 |
| EP | 3068888 | 1/2018 |
| EP | 3257600 | 1/2018 |
| EP | 3274453 | 1/2018 |
| EP | 3274454 | 1/2018 |
| EP | 3275894 | 1/2018 |
| EP | 278108 | 2/2018 |
| EP | 3279315 | 2/2018 |
| EP | 3286214 | 2/2018 |
| EP | 2289535 | 3/2018 |
| EP | 2545068 | 3/2018 |
| EP | 2675540 | 3/2018 |
| EP | 2750683 | 3/2018 |
| EP | 2796102 | 3/2018 |
| EP | 3066201 | 3/2018 |
| EP | 3066998 | 3/2018 |
| EP | 3107552 | 3/2018 |
| EP | 3288660 | 3/2018 |
| EP | 3288683 | 3/2018 |
| EP | 3289362 | 3/2018 |
| EP | 3291842 | 3/2018 |
| EP | 3291852 | 3/2018 |
| EP | 3292142 | 3/2018 |
| EP | 3292195 | 3/2018 |
| EP | 3292515 | 3/2018 |
| EP | 3294343 | 3/2018 |
| EP | 3294764 | 3/2018 |
| EP | 3294857 | 3/2018 |
| EP | 3294871 | 3/2018 |
| EP | 3294888 | 3/2018 |
| EP | 3294896 | 3/2018 |
| EP | 3296302 | 3/2018 |
| EP | 3297740 | 3/2018 |
| EP | 3298046 | 3/2018 |
| EP | 3164488 | 4/2018 |
| EP | 3301115 | 4/2018 |
| EP | 3302783 | 4/2018 |
| EP | 3302789 | 4/2018 |
| EP | 3303558 | 4/2018 |
| EP | 3306310 | 4/2018 |
| EP | 2675901 | 5/2018 |

(56) References Cited

FOREIGN PATENT DOCUMENTS

| | | |
|---|---|---|
| EP | 2956772 | 5/2018 |
| EP | 3323444 | 5/2018 |
| EP | 3324996 | 5/2018 |
| EP | 3327127 | 5/2018 |
| EP | 3337819 | 6/2018 |
| EP | 2772196 | 8/2018 |
| EP | 2882091 | 8/2018 |
| EP | 2910568 | 8/2018 |
| EP | 3265805 | 8/2018 |
| EP | 3359676 | 8/2018 |
| EP | 3360955 | 8/2018 |
| EP | 3361252 | 8/2018 |
| EP | 3362102 | 8/2018 |
| EP | 3363456 | 8/2018 |
| EP | 3363813 | 8/2018 |
| EP | 3365062 | 8/2018 |
| EP | 3365095 | 8/2018 |
| EP | 3365441 | 8/2018 |
| EP | 3365447 | 8/2018 |
| EP | 3366696 | 8/2018 |
| EP | 3367118 | 8/2018 |
| EP | 2931892 | 9/2018 |
| EP | 3019606 | 9/2018 |
| EP | 3089800 | 9/2018 |
| EP | 3123534 | 9/2018 |
| EP | 3368528 | 9/2018 |
| EP | 3368670 | 9/2018 |
| EP | 3371295 | 9/2018 |
| EP | 3372813 | 9/2018 |
| EP | 3372814 | 9/2018 |
| EP | 2535355 | 1/2019 |
| EP | 2922902 | 1/2019 |
| EP | 3004338 | 1/2019 |
| EP | 3421975 | 1/2019 |
| EP | 3423092 | 1/2019 |
| EP | 3423580 | 1/2019 |
| EP | 3425386 | 1/2019 |
| EP | 3426271 | 1/2019 |
| EP | 3426372 | 1/2019 |
| EP | 3426375 | 1/2019 |
| EP | 3426690 | 1/2019 |
| EP | 3427815 | 1/2019 |
| EP | 3429753 | 1/2019 |
| EP | 3430050 | 1/2019 |
| EP | 3430134 | 1/2019 |
| EP | 3430146 | 1/2019 |
| EP | 3430463 | 1/2019 |
| EP | 3433363 | 1/2019 |
| EP | 3433366 | 1/2019 |
| EP | 3434774 | 1/2019 |
| EP | 3434776 | 1/2019 |
| EP | 2598533 | 2/2019 |
| EP | 2691422 | 2/2019 |
| EP | 2925431 | 2/2019 |
| EP | 3170185 | 2/2019 |
| EP | 3436030 | 2/2019 |
| EP | 3436196 | 2/2019 |
| EP | 3436575 | 2/2019 |
| EP | 3436579 | 2/2019 |
| EP | 3437740 | 2/2019 |
| EP | 3439698 | 2/2019 |
| EP | 3440191 | 2/2019 |
| EP | 3441468 | 2/2019 |
| EP | 3442598 | 2/2019 |
| EP | 3443002 | 2/2019 |
| EP | 3443084 | 2/2019 |
| EP | 3445407 | 2/2019 |
| EP | 3445848 | 2/2019 |
| EP | 3445853 | 2/2019 |
| EP | 3445856 | 2/2019 |
| EP | 2694091 | 3/2019 |
| EP | 3080260 | 3/2019 |
| EP | 3448291 | 3/2019 |
| EP | 3448995 | 3/2019 |
| EP | 3449850 | 3/2019 |
| EP | 3452133 | 3/2019 |
| EP | 3452499 | 3/2019 |
| EP | 3453406 | 3/2019 |
| EP | 3456339 | 3/2019 |
| EP | 3458081 | 3/2019 |
| EP | 3458083 | 3/2019 |
| EP | 3458104 | 3/2019 |
| EP | 3458105 | 3/2019 |
| EP | 3458107 | 3/2019 |
| EP | 3458108 | 3/2019 |
| EP | 3458590 | 3/2019 |
| EP | 3066115 | 4/2019 |
| EP | 3119807 | 4/2019 |
| EP | 3186281 | 4/2019 |
| EP | 3361252 | 4/2019 |
| EP | 3463433 | 4/2019 |
| EP | 3463660 | 4/2019 |
| EP | 3464198 | 4/2019 |
| EP | 3464594 | 4/2019 |
| EP | 3467276 | 4/2019 |
| EP | 3467491 | 4/2019 |
| EP | 3468225 | 4/2019 |
| EP | 3468351 | 4/2019 |
| EP | 3468594 | 4/2019 |
| EP | 3470089 | 4/2019 |
| EP | 3470519 | 4/2019 |
| EP | 3471621 | 4/2019 |
| EP | 3473707 | 4/2019 |
| EP | 2546144 | 5/2019 |
| EP | 3311588 | 5/2019 |
| EP | 3474904 | 5/2019 |
| EP | 3475307 | 5/2019 |
| EP | 3481361 | 5/2019 |
| EP | 3481867 | 5/2019 |
| EP | 2412817 | 6/2019 |
| EP | 3490562 | 6/2019 |
| EP | 3490574 | 6/2019 |
| EP | 3490694 | 6/2019 |
| EP | 3490712 | 6/2019 |
| EP | 3490801 | 6/2019 |
| EP | 3491124 | 6/2019 |
| EP | 3491126 | 6/2019 |
| EP | 3493836 | 6/2019 |
| EP | 3493907 | 6/2019 |
| EP | 3495376 | 6/2019 |
| EP | 3495811 | 6/2019 |
| EP | 3498846 | 6/2019 |
| EP | 3500244 | 6/2019 |
| EP | 3500271 | 6/2019 |
| EP | 3500297 | 6/2019 |
| EP | 3500659 | 6/2019 |
| EP | 3500696 | 6/2019 |
| EP | 3502137 | 6/2019 |
| EP | 3502253 | 6/2019 |
| GB | 2 420 510 A | 5/2006 |
| JP | H02-290266 | 11/1990 |
| JP | 9-136090 | 5/1997 |
| JP | H11-090110 | 4/1999 |
| JP | 2005-249267 | 12/2005 |
| KR | 1442486 | 9/2014 |
| RU | 2037327 C1 | 6/1995 |
| RU | 94015846 | 6/1996 |
| RU | 2067079 | 9/1996 |
| RU | 2085933 | 7/1997 |
| SU | 629496 | 10/1978 |
| WO | WO 1987/07178 A1 | 12/1987 |
| WO | WO 89/11899 A1 | 12/1989 |
| WO | WO 90/05008 | 3/1990 |
| WO | WO 95/01214 A1 | 1/1995 |
| WO | WO 97/34643 | 9/1997 |
| WO | WO 1998/017373 | 4/1998 |
| WO | WO 98/50133 A1 | 11/1998 |
| WO | WO 00/41794 | 7/2000 |
| WO | WO 02/072234 A1 | 9/2002 |
| WO | WO 02/072236 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |

(56) References Cited

FOREIGN PATENT DOCUMENTS

| | | |
|---|---|---|
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/130321 | 10/2011 |
| WO | WO 2011/131947 A2 | 10/2011 |
| WO | WO 2011/161463 A2 | 12/2011 |
| WO | WO 2013/043044 A1 | 3/2013 |
| WO | WO 2013/043046 | 3/2013 |
| WO | WO 2013/043297 A1 | 3/2013 |
| WO | WO 2013030691 | 3/2013 |
| WO | WO 2013/049623 A1 | 4/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/035457 | 3/2014 |
| WO | WO 2014/046605 A1 | 3/2014 |
| WO | WO 2014/055219 A2 | 4/2014 |
| WO | WO 2014/124306 A1 | 8/2014 |
| WO | WO 2014/153651 | 10/2014 |
| WO | WO 2014/165177 | 10/2014 |
| WO | WO 2015/006730 | 1/2015 |
| WO | WO 2015/102528 | 7/2015 |
| WO | WO 2016/004398 A2 | 1/2016 |
| WO | WO 2016/124542 | 8/2016 |
| WO | WO 2016/176663 | 11/2016 |
| WO | WO 2016/209082 | 12/2016 |
| WO | WO 2017/011519 | 1/2017 |
| WO | WO 2017/021543 | 2/2017 |
| WO | WO 2017/041102 | 3/2017 |
| WO | WO 20174201349 | 11/2017 |
| WO | WO 2017218714 | 12/2017 |
| WO | WO 2018/009894 A1 | 1/2018 |
| WO | WO 2018002036 | 1/2018 |
| WO | WO 2018005873 | 1/2018 |
| WO | WO 2018013558 | 1/2018 |
| WO | WO 2018013629 A1 | 1/2018 |
| WO | WO 2018013840 | 1/2018 |
| WO | WO2018014174 | 1/2018 |
| WO | WO2018015561 | 1/2018 |
| WO | WO 20180011600 | 1/2018 |
| WO | WO2018018958 | 2/2018 |
| WO | WO2018021920 | 2/2018 |
| WO | WO2018022158 | 2/2018 |
| WO | WO 2018022513 | 2/2018 |
| WO | WO2018022619 | 2/2018 |
| WO | WO2018022651 | 2/2018 |
| WO | WO2018022930 | 2/2018 |
| WO | WO2018023114 | 2/2018 |
| WO | WO2018024639 | 2/2018 |
| WO | WO2018026644 | 2/2018 |
| WO | WO2018026941 | 2/2018 |
| WO | WO2018028647 | 2/2018 |
| WO | WO 2018034343 | 2/2018 |
| WO | WO2018034885 | 2/2018 |
| WO | WO 2018035141 | 2/2018 |
| WO | WO 2018035423 | 2/2018 |
| WO | WO20180202691 | 2/2018 |
| WO | WO 2018034655 | 3/2018 |
| WO | WO 2018038711 | 3/2018 |
| WO | WO 2018039119 | 3/2018 |
| WO | WO 2018039407 | 3/2018 |
| WO | WO 2018039408 | 3/2018 |
| WO | WO 2018039410 | 3/2018 |
| WO | WO 2018039412 | 3/2018 |
| WO | WO 2018039515 | 3/2018 |
| WO | WO 2018045284 | 3/2018 |
| WO | WO 2018049226 | 3/2018 |
| WO | WO 2018050738 | 3/2018 |
| WO | WO 2018057825 | 3/2018 |
| WO | WO 2018063291 | 4/2018 |
| WO | WO 2018058275 | 5/2018 |
| WO | WO 2018081476 | 5/2018 |
| WO | WO 2018091879 | 5/2018 |
| WO | WO2018094244 | 5/2018 |
| WO | WO 20180814701 | 5/2018 |
| WO | WO 2018098671 | 6/2018 |
| WO | WO 2018102752 | 6/2018 |
| WO | WO 2018106163 | 6/2018 |
| WO | WO 2018112145 | 6/2018 |
| WO | WO 2018112335 | 6/2018 |
| WO | WO 2018138385 | 8/2018 |
| WO | WO 2018140573 | 8/2018 |
| WO | WO 2018140845 | 8/2018 |
| WO | WO 2018142364 | 8/2018 |
| WO | WO 2018151811 | 8/2018 |
| WO | WO 2018151823 | 8/2018 |
| WO | WO 2018153772 | 8/2018 |
| WO | WO 2018160548 | 9/2018 |
| WO | WO 2018160909 | 9/2018 |
| WO | WO 2018160993 | 9/2018 |
| WO | WO 2018161017 | 9/2018 |
| WO | WO 2018161026 | 9/2018 |
| WO | WO 2018161038 | 9/2018 |
| WO | WO 2018161905 | 9/2018 |
| WO | WO 2018163183 | 9/2018 |
| WO | WO2018227286 | 12/2018 |
| WO | WO2018229612 | 12/2018 |
| WO | WO2018231990 | 12/2018 |
| WO | WO2018232045 | 12/2018 |
| WO | WO2018232131 | 12/2018 |
| WO | WO2018234421 | 12/2018 |
| WO | WO2018235228 | 12/2018 |
| WO | WO2018236708 | 12/2018 |
| WO | WO2018237201 | 12/2018 |
| WO | WO2018237239 | 12/2018 |
| WO | WO2018183966 | 1/2019 |
| WO | WO2019002551 | 1/2019 |
| WO | WO2019002633 | 1/2019 |
| WO | WO2019005155 | 1/2019 |
| WO | WO2019005866 | 1/2019 |
| WO | WO2019005871 | 1/2019 |
| WO | WO2019006418 | 1/2019 |
| WO | WO2019007869 | 1/2019 |
| WO | WO2019008335 | 1/2019 |
| WO | WO2019010422 | 1/2019 |
| WO | WO2019018423 | 1/2019 |
| WO | WO2019018491 | 1/2019 |
| WO | WO2019018796 | 1/2019 |
| WO | WO2019022671 | 1/2019 |
| WO | WO2019023523 | 1/2019 |
| WO | WO2019025661 | 2/2019 |
| WO | WO2019025984 | 2/2019 |
| WO | WO2019028172 | 2/2019 |
| WO | WO2019032675 | 2/2019 |
| WO | WO2019036382 | 2/2019 |
| WO | WO209048639 | 3/2019 |
| WO | WO2019041344 | 3/2019 |
| WO | WO2019046450 | 3/2019 |
| WO | WO2019048666 | 3/2019 |
| WO | WO2019051106 | 3/2019 |
| WO | WO2019051255 | 3/2019 |
| WO | WO2019051278 | 3/2019 |
| WO | WO2019051316 | 3/2019 |
| WO | WO2019051355 | 3/2019 |
| WO | WO2019055697 | 3/2019 |
| WO | WO2019055817 | 3/2019 |
| WO | WO2019055896 | 3/2019 |
| WO | WO2019056015 | 3/2019 |
| WO | WO2019057774 | 3/2019 |
| WO | WO2019058321 | 3/2019 |
| WO | WO2019058326 | 3/2019 |
| WO | WO2019060253 | 3/2019 |
| WO | WO2019060425 | 3/2019 |
| WO | WO2019060779 | 3/2019 |
| WO | WO2019067015 | 4/2019 |
| WO | WO2019069101 | 4/2019 |
| WO | WO2019070541 | 4/2019 |
| WO | WO2019070974 | 4/2019 |

(56) References Cited

FOREIGN PATENT DOCUMENTS

| WO | WO2019072889 | 4/2019 |
|---|---|---|
| WO | WO2019075409 | 4/2019 |
| WO | WO2019079497 | 4/2019 |
| WO | WO2019079819 | 4/2019 |
| WO | WO2019080898 | 5/2019 |
| WO | WO2019081521 | 5/2019 |
| WO | WO2019094360 | 5/2019 |
| WO | WO2019098839 | 5/2019 |
| WO | WO2019099619 | 5/2019 |
| WO | WO2019099736 | 5/2019 |
| WO | WO2019099949 | 5/2019 |
| WO | WO2019101691 | 5/2019 |
| WO | WO2019101956 | 5/2019 |
| WO | WO2018215686 | 6/2019 |
| WO | WO2019111250 | 6/2019 |
| WO | WO2019113310 | 6/2019 |
| WO | WO2019118475 | 6/2019 |
| WO | WO2018231759 | 12/2019 |

OTHER PUBLICATIONS

Augustsson et al., Acoustophoretic microfluidic chip for sequential elution of surface bound molecules from beads or cells, Biomicrofluidics, sep. 2012, 6(3):34115.

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

Chitale et al.; Understanding the Fluid Dynamics Associated with Macro Scale Ultrasonic Separators; Proceedings of Meetings on Acoustics, May 2015.

Cravotto et al.; Ultrasonics Sonochemistry, vol. 15, No. 5, pp. 898-902, 2008.

Ding, X et al., "Cell Separation Using Tilted-Angle Standing Surface Acoustic Waves", Proceedings of the National Academy of Sciences, Sep. 9, 2014, vol. 111, No. 36, pp. 12992-12997, See abstract; p. 12994, left column page 12995, left column; figure 1-3 and 6.

Ensminger et al; Ultrasonics Fundamentals, Technologies, and Applications; 2011.

Evander et al; Acoustofluidics 20: Applications in acoustic trapping, Lab Chip, 2012,12,4667-4676.

Evander et al; Acoustiofluidics 5: Building microfluidic acoustic resonators, Lab Chip, 2012, 12, 684.

Gallego-Juarez et al; "Piezoelectric ceramic and ultrasonic transducers"; Journal of Physics E: Scientific Instruments. 1989.

Ganguly et al; Essential Physics for Radiology and Imaging; Academic Publishers, Jan. 2016.

Garcia-Lopez, et al; Enhanced Acoustic Separation of Oil-Water Emulsion in Resonant Cavities. The Open Acoustics Journal. 2008, vol. 1, pp. 66-71.

Greenhall et al; Dynamic behavior of microscale particles controlled by standing bulk acoustic waves; Applied Physics Letters, 105, 144105 (2014).

Grenvall et al.; Concurrent Isolation of Lymphocytes and Granulocytes Using Prefocused Free Flow Acoustophoresis; Analytical Chemistry; vol. 87; pp. 5596-5604; 2015.

Gorenflo et al; Characterization and Optimization of Acoustic Filter Performance by Experimental DesignMethodology (whole document).

Gor'Koy et al; On the Forces Acting on a Small Particle in an Acoustical Field in an Ideal Fluid; Soviet Physics Doklady, vol. 6, p. 773.

Higginson et al.; Tunable optics derived from nonlinear acoustic effects; Journal of Applied Physics; vol. 95; No. 10; pp. 5896-5904; 2004.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Jin et al; Pharmaceutical Engineering; Jan. 2015; vol. 35 No. 1.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Li et al.; Electromechanical behavior of PZT-brass unimorphs; J. Am. Ceram. Soc. vol. 82; No. 7; pp. 1733-1740, 1999.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; Separation of bacterial spores from flowering water in macro-scale cavities by ultrasonic standing waves; submitted/uploaded to http://arxiv.org/abs/1006.5467 on Jun. 28, 2010.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et al.; An Industrial-Prototype Acoustic Array for Real-Time Emulsion Layer Detection in Oil Storage Tanks; IEEE Sensors Journal, vol. 9, No. 12, Dec. 2009.

Musiak et al.; Design of a Control System for Acoustophoretic Separation, 2013 IEEE 56th International Midwest Symposium on Circuits and Systems (MWSCAS), Aug. 2013, pp. 1120-1123.

National Science Foundation, "Catalyzing Commercialization: putting sound to work for challenging separations", CEP, Sep. 2015, p. 14.

Nilsson et al.; Review of cell and particle trapping in microfluidic systems; Department of Measurement Technology and Industrial Electrical Engineering, Div. Of Nanobiotechnology, Lund University, P.O. Box 118. Lund, Sweden, Analytica Chimica Acta 649, Jul. 14, 2009, pp. 141-157.

Nienow et al.; A potentially scalable method for the harvesting of hMSCs from microcarriers; Biochemical Engineering Journal 85 (2014) 79-88.

Pangu et al.; Droplet transport and coalescence kinetics in emulsions subjected to acoustic fields; Ultrasonics 46, pp. 289-302 (2007).

Phys. Org. "Engineers develop revolutionary nanotech water desalination membrane." Nov. 6, 2006. http://phys.org/news82047372.html.

Ponomarenko et al.; Density of states and zero Landau level probed through capacitance of graphene; Nature Nanotechnology Letters, Jul. 5, 2009; DOI: 10.1038/NNANO.2009.177.

"Proceedings of the Acoustics 2012 Nantes Conference," Apr. 23-27, 2012, Nantes, France, pp. 278-282.

Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.

Seymour et al, J. Chem. Edu., 1990, 67(9), p. 763, published Sep. 1990.

Shitizu et al; "A Tutorial Review on Bioprocessing Systems Engineering" (whole document).

Volpin et al.; Mesh simplification with smooth surface reconstruction; Computer-Aided Design; vol. 30; No. 11; 1998.

(56) References Cited

OTHER PUBLICATIONS

Wang et al.; Retention and Viability Characteristics of Mammalian Cells in an Acoustically Driven Polymer Mesh; Biotechnol. Prog. 2004, pp. 384-387 (2004).
Wicklund et al.; Ultrasonic Manipulation of Single Cells; Methods in Molecular Biology; vol. 853; pp. 1777-196; 2012.
Woodside et al; Acoustic Force Distribution in Resonators for Ultrasonic Particle Separation; Biotechnology Laboratory and Dept of Chemical and Bio-Resource Engineering, University of British Columbia, Sep. 1998, vol. 44, No. 9.
Zhanqiu et al ;Culture Conditions and Types of Growth Media for Mammalian Cells (whole document).
Annex to Form PCT/ISA/206—Communication Relating to the Results of the Partial International Search Report dated Jul. 18, 2013.
European Search Report of European Application No. 11769474.5 dated Sep. 5, 2013.
European Search Report of European Application No. 11796470.0 dated Jan. 5, 2016.
European Search Report of European Application No. 13760840.2, dated Feb. 4, 2016.
European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.
International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 dated Jun. 21, 2013.
International Search Report and Written Opinion for International Application No. PCT/US2013/032705 dated Jul. 26, 2013.
International Search Report and Written Opinion for International Application No. PCT/US2013/050729 dated Sep. 25, 2013.
International Search Report and Written Opinion for International Application No. PCT/US2013/059640 dated Feb. 18, 2014.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
International Search Report and Written Opinion for International Application No. PCT/US2017/030903 dated Jul. 19, 2017.
International Search Report and Written Opinion for International Application No. PCT/US2017/025108 dated Jul. 20, 2017.
International Search Report and Written Opinion for International Application No. PCT/US2017/031425 dated Aug. 30, 2017.
Sony New Release: <http://www.sony.net/SonyInfo/News/Press/201010/10-137E/index.html>.
International Search Report and Written Opinion for International Application No. PCT/US2017/031425 dated Oct. 23, 2017.
International Search Report and Written Opinion for International Application No. PCT/US2018/026617, dated Jul. 4, 2018.
International Search Report and Written Opinion for International Application No. PCT/US2018/31267, dated Aug. 1, 2018.
European Search Report of European Application No. 15847217.5 dated Oct. 15, 2018.
International Search Report and Written Opinion for International Application No. PCT/US2017/057485, dated Apr. 23, 2019.
International Search Report and Written Opinion for International Application No. PCT/US18/65839, dated May 16, 2019.
International Search Report and Written Opinion for International Application No. PCT/US19/12950, dated May 24, 2019.
International Search Report and Written Opinion for International Application No. PCT/US18/63698, dated May 27, 2019.
International Search Report and Written Opinion for International Application No. PCT/US19/21492, dated Jun. 25, 2019.

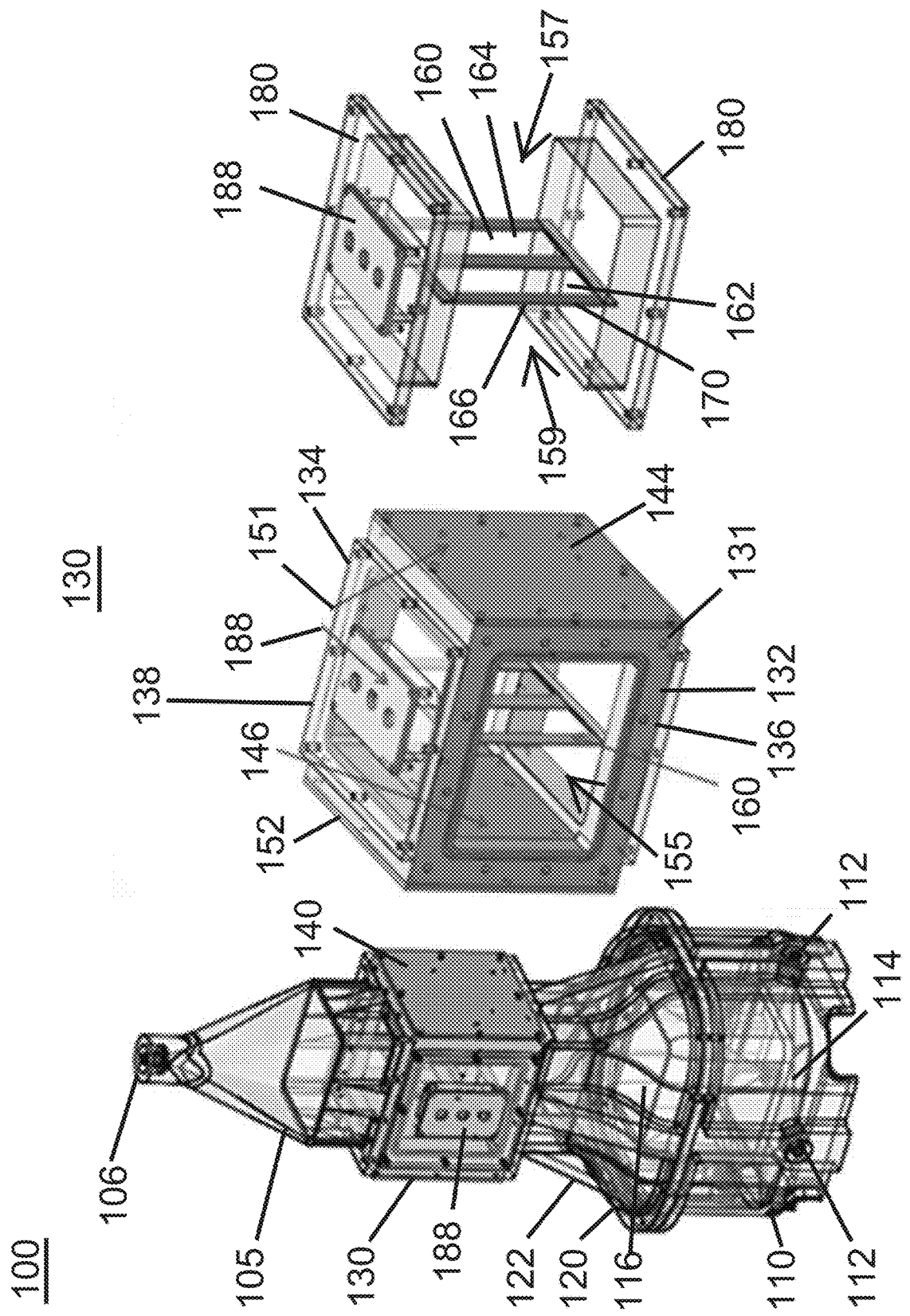

ACOUSTOPHORESIS DEVICE WITH DUAL ACOUSTOPHORETIC CHAMBER

CROSS-REFERENCE TO RELATED APPLICATIONS

This application is a divisional of U.S. patent application Ser. No. 14/592,337, filed Jan. 8, 2015, which claims priority to U.S. Provisional Patent Application Ser. No. 61/925,171, filed Jan. 8, 2014. The disclosures of this application is hereby fully incorporated by reference in its entirety.

BACKGROUND

The ability to separate a particle/fluid mixture into its separate components is desirable in many applications. Acoustophoresis is the separation of particles using high intensity sound waves, and without the use of membranes or physical size exclusion filters. It has been known that high intensity standing waves of sound can exert forces on particles in a fluid when there is a differential in both density and compressibility, otherwise known as the contrast factor. A standing wave has a pressure profile which appears to "stand" still in time. The pressure profile in a standing wave contains areas of net zero pressure at its nodes and anti-nodes. Depending on the density and compressibility of the particles, they will be trapped at the nodes or anti-nodes of the standing wave. The higher the frequency of the standing wave, the smaller the particles that can be trapped.

Conventional acoustophoresis devices have had limited efficacy due to several factors including heat generation, limits on fluid flow, and the inability to capture different types of materials. In particular, heat generation can be deleterious to materials in the fluid stream, particularly in biopharmaceutical applications when materials such as Chinese hamster ovary (CHO) cells and proteins and monoclonal antibodies expressed therefrom are present in the fluid stream.

In this regard, an ultrasonic transducer including a piezoelectric element has typically been used to generate ultrasonic waves. The transducer is generally mounted into the wall of a chamber, with a reflector mounted in the opposite wall. The face of the reflector is parallel to the face of the piezoelectric element, maximizing reflection of the incident wave generated from the piezoelectric element to form the standing wave. Heat is generated by the piezoelectric element during operation when performing acoustophoresis. It would be desirable to provide alternative designs that minimize heat generation.

BRIEF SUMMARY

The present disclosure relates to acoustophoretic systems that include a piezoelectric element in the middle of a flow path, rather than to one side of the flow path. This permits both sides of the piezoelectric element to generate an acoustic standing wave, rather than only one side of the element. This also permits both sides to be exposed to the fluid stream and the resulting cooling effect, mitigating heat buildup in the piezoelectric element. This device can be used to separate particles from a particle/fluid mixture. Either a new mixture with an increased concentration of particles can be obtained, or the separated particles themselves can be obtained. In more specific embodiments, the particles are biological cells, such as Chinese hamster ovary (CHO) cells, NS0 hybridoma cells, baby hamster kidney (BHK) cells, and human cells. Several different types of modules and overall systems are described herein.

Disclosed in various embodiments herein is an acoustophoresis device, comprising: a device inlet permitting fluid flow into the device; a device outlet permitting fluid egress from the device; and an acoustic chamber located in a fluid path between the device inlet and the device outlet. The acoustic chamber comprises: a first end and a second end opposite the first end; a piezoelectric element running between the first end and the second end, and separating the acoustic chamber into a first flow chamber and a second flow chamber, the piezoelectric element having a first face and a second face; a first reflector opposite the first face of the piezoelectric element, the first flow chamber being located between the first reflector and the first face; and a second reflector opposite the second face of the piezoelectric element, the second flow chamber being located between the second reflector and the second face.

The acoustic chamber can further comprise: a holding plate that holds the piezoelectric element, and two bracket plates having a slot for maintaining the holding plate in a fixed location in the acoustic chamber.

The piezoelectric element may include a plurality of piezoelectric crystals. Generally, the piezoelectric element is adapted to create a multi-dimensional standing wave in the first flow chamber and the second flow chamber. In more specific embodiments, different standing waves (e.g. of different frequencies) are generated in the first flow chamber and the second flow chamber by the piezoelectric element.

In some embodiments, the acoustophoresis device is shaped such that fluid flows into the device through the device inlet, into the first end of the acoustic chamber, then flows in parallel through the first flow chamber and the second flow chamber, out of the acoustic chamber through the second end of the acoustic chamber, and out of the device through the device outlet. The acoustophoresis device can further comprise a contoured nozzle wall between the device inlet and the acoustic chamber.

In other embodiments, the acoustophoresis device is shaped such that fluid flows into the device through the device inlet, then travels through the acoustic chamber in a U-shaped path from the first end of the acoustic chamber to the second end through the first flow chamber and then back to the first end through the second flow chamber, then exits the flow chamber through the first end of the acoustic chamber and exits the device through the device outlet. In such embodiments, the second end of the acoustic chamber may lead to a well that tapers downwards in cross-sectional area from a single inlet to a vertex, and a drain line connecting the vertex to a port for recovering material collected in the well.

Also disclosed are methods of separating particles from a host fluid, comprising: flowing a mixture of the host fluid and the particles through an acoustophoresis device as described above, having a first flow chamber and a second flow chamber. A pulsed voltage signal drives the piezoelectric element to create multidimensional standing waves in the first flow chamber and the second flow chamber to separate the particles from the host fluid.

The multi-dimensional standing waves may result in an acoustic radiation force having an axial force component and a lateral force component that are of the same order of magnitude, in both the first flow chamber and the second flow chamber.

In particular embodiments, the particles are Chinese hamster ovary (CHO) cells, NS0 hybridoma cells, baby hamster kidney (BHK) cells, or human cells.

The pulsed voltage signal may have a sinusoidal, square, sawtooth, or triangle waveform. The pulsed voltage signal may have a frequency of 500 kHz to 10 MHz. The pulsed voltage signal can be driven with amplitude or frequency modulation start/stop capability to eliminate acoustic streaming.

In particular embodiments, the mixture of the host fluid and the particles has a Reynolds number of 1500 or less prior to entering the acoustic chamber. Sometimes, the mixture flows vertically upwards, and the particles sink down to a collection duct.

Also disclosed in various embodiments herein is an acoustophoresis device, comprising: a device inlet permitting fluid flow into the device; a device outlet permitting fluid egress from the device; and an acoustic chamber located in a fluid path between the device inlet and the device outlet. The acoustic chamber comprises a plurality of piezoelectric elements running between the first end and the second end; and a plurality of reflectors. Each piezoelectric element has a first face and a second face; and each element is located between two reflectors.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 1 is an exterior perspective view of an acoustophoresis device including the "dual acoustophoresis chamber" of the present disclosure. Visible in this view is a connector panel for powering the piezoelectric element.

FIG. 2 is a perspective view of the dual acoustophoresis chamber only, with the connector panel at the top of the figure.

FIG. 3 is a perspective view of the holding plate that holds the piezoelectric element located between two bracket plates which hold the holding plate in place within the acoustic chamber.

DETAILED DESCRIPTION

Figure 4:
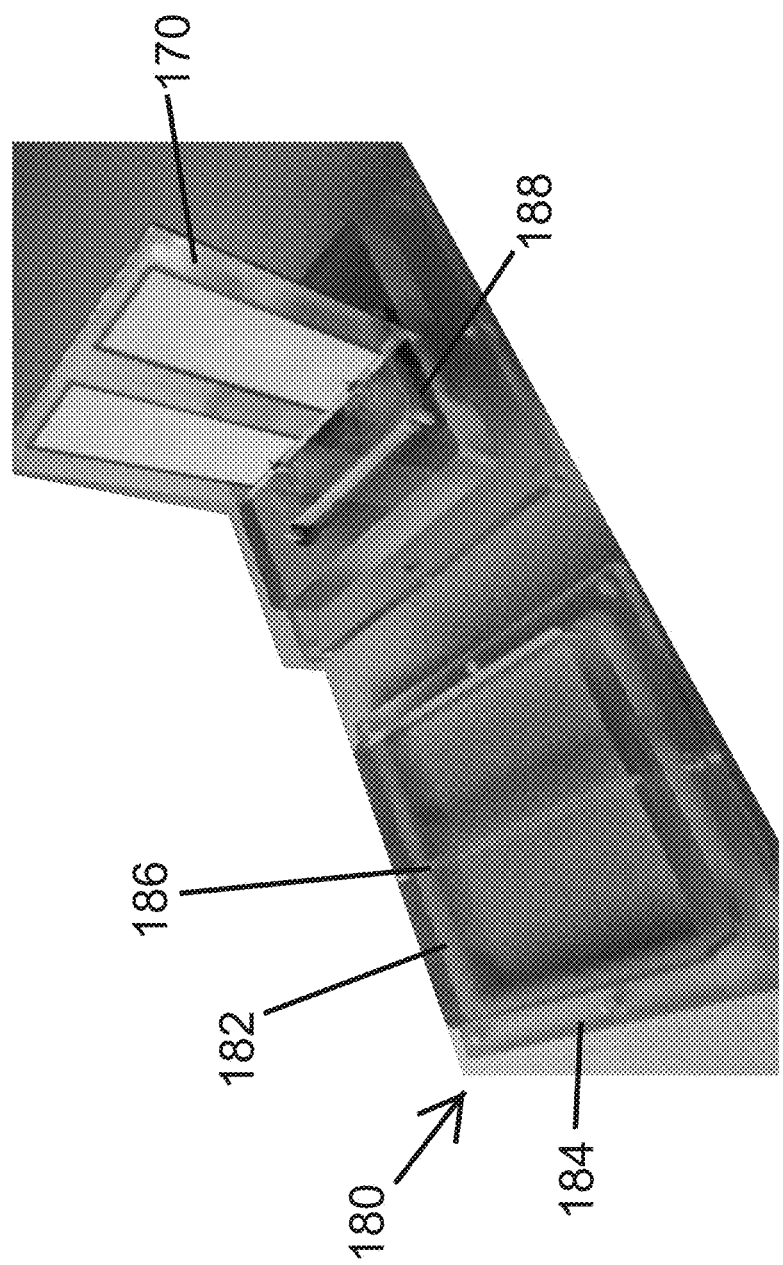
FIG. 4 is a picture showing the holding plate and the bracket plates. The piezoelectric element is made up of two separate rectangular piezoelectric crystals.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, along with any impurities that might result therefrom, and excludes other components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value less than 10.

The acoustophoretic separation technology of the present disclosure employs ultrasonic standing waves to trap, i.e., hold stationary, secondary phase particles in a host fluid stream. This is an important distinction from previous approaches where particle trajectories were merely altered by the effect of the acoustic radiation force. The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy and gravitational force, the particle is trapped within the acoustic standing wave field. This results in concentration, agglomeration and/or coalescence of the trapped particles. Additionally, secondary inter-particle forces, such as Bjerkness forces, aid in particle agglomeration. Heavier-than-the-host-fluid (i.e. denser than the host fluid) particles are separated through enhanced gravitational settling.

One specific application for the acoustophoresis device is in the processing of bioreactor materials. It is important to be able to filter all of the cells and cell debris from the expressed materials that are in the fluid stream. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over current filtration processes (depth filtration, tangential flow filtration, centrifugation), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, and human cells has proven to be a very efficacious way of producing/expressing the recombinant proteins and monoclonal antibodies required of today's pharmaceuticals. The filtration of the mammalian cells and the mammalian cell debris through acoustophoresis aids in greatly increasing the yield of the bioreactor.

In this regard, the contrast factor is the difference between the compressibility and density of the particles and the fluid itself. These properties are characteristic of the particles and the fluid themselves. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles with a negative contrast factor are driven to the pressure anti-nodal planes. The radial or lateral component of the acoustic radiation force helps trap the cells. The radial or lateral component of the ARF is larger than the combined effect of fluid drag force and gravitational force.

As the cells agglomerate at the nodes of the standing wave, there is also a physical scrubbing of the cell culture media that occurs whereby more cells are trapped as they come in contact with the cells that are already held within the standing wave. This generally separates the cells from the cell culture media. The expressed biomolecules remain in the nutrient fluid stream (i.e. cell culture medium).

Desirably, the ultrasonic transducer(s) generate a three-dimensional or multi-dimensional acoustic standing wave in the fluid that exerts a lateral force on the suspended particles to accompany the axial force so as to increase the particle trapping capabilities of the standing wave. Typical results published in literature state that the lateral force is two orders of magnitude smaller than the axial force. In contrast, the technology disclosed in this application provides for a lateral force to be of the same order of magnitude as the axial force.

It is also possible to drive multiple ultrasonic transducers with arbitrary phasing. In other words, the multiple transducers may work to separate materials in a fluid stream while being out of phase with each other. Alternatively, a single ultrasonic transducer that has been divided into an ordered array may also be operated such that some components of the array will be out of phase with other components of the array.

Three-dimensional (3-D) or multi-dimensional acoustic standing waves are generated from one or more piezoelectric transducers, where the transducers are electrically or mechanically excited such that they move in a multi-excitation mode. The types of waves thus generated can be characterized as composite waves, with displacement profiles that are similar to leaky symmetric (also referred to as compressional or extensional) Lamb waves. The waves are leaky because they radiate into the water layer, which result in the generation of the acoustic standing waves in the water layer. Symmetric Lamb waves have displacement profiles that are symmetric with respect to the neutral axis of the piezoelectric element, which causes multiple standing waves to be generated in a 3-D space. Through this manner of wave generation, a higher lateral trapping force is generated than if the piezoelectric transducer is excited in a "piston" mode where only a single, planar standing wave is generated. Thus, with the same input power to a piezoelectric transducer, the 3-D or multi-dimensional acoustic standing waves can have a higher lateral trapping force which may be up to and beyond 10 times stronger than a single acoustic standing wave generated in piston mode.

It may be necessary, at times, due to acoustic streaming, to modulate the frequency or voltage amplitude of the standing wave. This may be done by amplitude modulation and/or by frequency modulation. The duty cycle of the propagation of the standing wave may also be utilized to achieve certain results for trapping of materials. In other words, the acoustic beam may be turned on and shut off at different frequencies to achieve desired results.

Some of the variables that are involved in the generation of a standing wave using piezoelectric crystals are voltage input, the Q factor of the piezoelectric crystal, the impedance of the full transducer that incorporates the piezoelectric crystal, and the temperature or heat generated by the piezoelectric crystal/transducer during the operation of the unit when performing acoustophoresis. As previously discussed, heat can be deleterious to materials in the fluid, such as biological cells or products. Prior devices have used various methods and fluid flow patterns to dissipate heat generated during acoustophoresis, or have modulated perturbation of the piezoelectric crystal to mitigate heat input into the system.

The present disclosure relates to acoustophoretic devices where the piezoelectric element that generates the standing wave is placed in the volume of the acoustic chamber, such that a fluid/particle mixture flows on both sides of the piezoelectric element and standing waves can be generated on both sides of the piezoelectric element. This may also be referred to as a "dual acoustophoresis chamber". The cooling effect of fluid flow on both sides mitigates heat buildup that may occur in the piezoelectric element. The fluid can be a liquid (e.g. water) or can be a gas (e.g. air).

FIG. 1 is an exterior perspective view of a basic acoustophoresis device 100 that includes the dual acoustophoresis chamber. The basic device here is illustrated as being formed from separate components. These components include an inlet module 110, a connecting module 120, the acoustic chamber 130, and an outlet module 105. Two exterior walls of the acoustic chamber can be seen. On one wall is a reflector 144, and on the other wall is a connector panel 188 for powering the piezoelectric element (not visible) inside the acoustic chamber.

In FIG. 1, fluid flow is upwards. Briefly, the inlet module contains inlets 112 that feed into an annular plenum 114. A fluid/particle mixture is pumped in through the inlets. The mixture flows upwards under pressure into the connecting module 120, which has a contoured nozzle wall 122 that reduces the cross-section of the fluid flow path. As fluid continues to be pumped into the flow path, eventually the inlet module 110 and the acoustic chamber 130 are filled with fluid, and the fluid pressure rises high enough that fluid will flow out through the outlet 106 at the top of the device. The particles within the ultrasonic standing wave collect or agglomerate, and eventually grow to a size where gravity overcomes the acoustic force of the standing wave, and the particle aggregates then fall/sink through a collection duct 116 that is surrounded by the annular plenum 114. The particles can then be collected, either as a more concentrated fluid/particle mixture or simply the particles themselves are collected.

FIG. 2 is a perspective view of the acoustic chamber of FIG. 1. The acoustic chamber 130 includes a housing 131 having a first end 132 and a second end 134 which are located at opposite ends of the housing. Here, the housing is in the shape of a cube having four side walls 151, 152 (third and fourth side walls not visible), a first wall 136, and a second wall 138. However, the exterior shape of the module is not particularly relevant, and could be for example cylindrical. The first end and the second end of the housing can be considered as defining a z-axis. The four opposing side walls can be considered as corresponding to opposite directions along the x-y axes of the housing.

A flow channel 155 is defined between the first end 132 and the second end 134 of the housing. Put another way, an opening is present in both the first wall and the second wall, and a bore joins the two openings together, such that fluid can flow through the housing from between the first end and the second end. As illustrated here, the bore has a rectangular cross-section. The piezoelectric element is located within the volume of the flow channel. As illustrated here, there are two reflectors 144, 146, which are located on opposite sides of the piezoelectric element 160. The faces of the two reflectors are parallel to the two faces of the piezoelectric element. Each reflector is solid or flexible, and can be made of a high acoustic impedance material such as steel or tungsten, providing good reflection. Also visible is the connector panel 188 on another side wall of the housing. The connectors can be any suitable type, such as BNC connectors.

FIG. 3 is a perspective view of specific portions of the acoustic chamber. In this regard, the piezoelectric element 160 is located within the volume of the acoustic chamber. The combination of the piezoelectric element 160, the first reflector 144, and the second reflector 146 divides the acoustic chamber 130 and the flow channel 155 into a first flow chamber 157 and a second flow chamber 159. As depicted here, the piezoelectric element 160 is comprised of two rectangular piezoelectric crystals 162. Generally, any number of piezoelectric crystals can be used to make up the piezoelectric element, and those crystals can be oriented in any direction relative to each other. The piezoelectric crystals are held in place by a holding plate 170. The holding plate is itself held in place by two bracket plates 180.

The piezoelectric element 160 has a first face 164 and a second face 166. Examining FIG. 2 and FIG. 3 together, there is a first reflector 144 opposite the first face 164. The first flow chamber 157 is located between the first reflector and the first face. Similarly, there is a second reflector 146 opposite the second face 166, with the second flow chamber 159 being located therebetween. Please note the location of the reflectors 144, 146 is based on the location of the piezoelectric element 160; the reflectors do not need to be set in the walls of the housing, as will be seen further below. However, generally, the faces of the piezoelectric element are parallel to the walls of the acoustic chamber, and reflectors are also located in opposite walls of the acoustic chamber, the reflectors being parallel to the faces of the piezoelectric element.

FIG. 4 is a photograph showing a bracket plate (left side) 180 separated from the holding plate 170. It is noted that the bracket plates are solid pieces; fluid does not flow through them. As depicted here, each bracket plate 180 includes a central block 182 and an edge plate 184 around its periphery, to connect the bracket plate to the housing. The edge plate 184 may not be needed in different embodiments, for example where the housing is of a different shape such that only the central block 182 is needed to connect to the housing. The central block 182 of each bracket plate also contains at least one slot 186, into which an edge of the holding plate 170 is inserted to fix the holding plate in a stationary position within the volume of the acoustic chamber. As discussed further below, a reflector can also be fixed within a slot. The bracket plate on the right side holds the holding plate 170, and also provides the connector panel 188 for powering the piezoelectric element.

Figure 5:
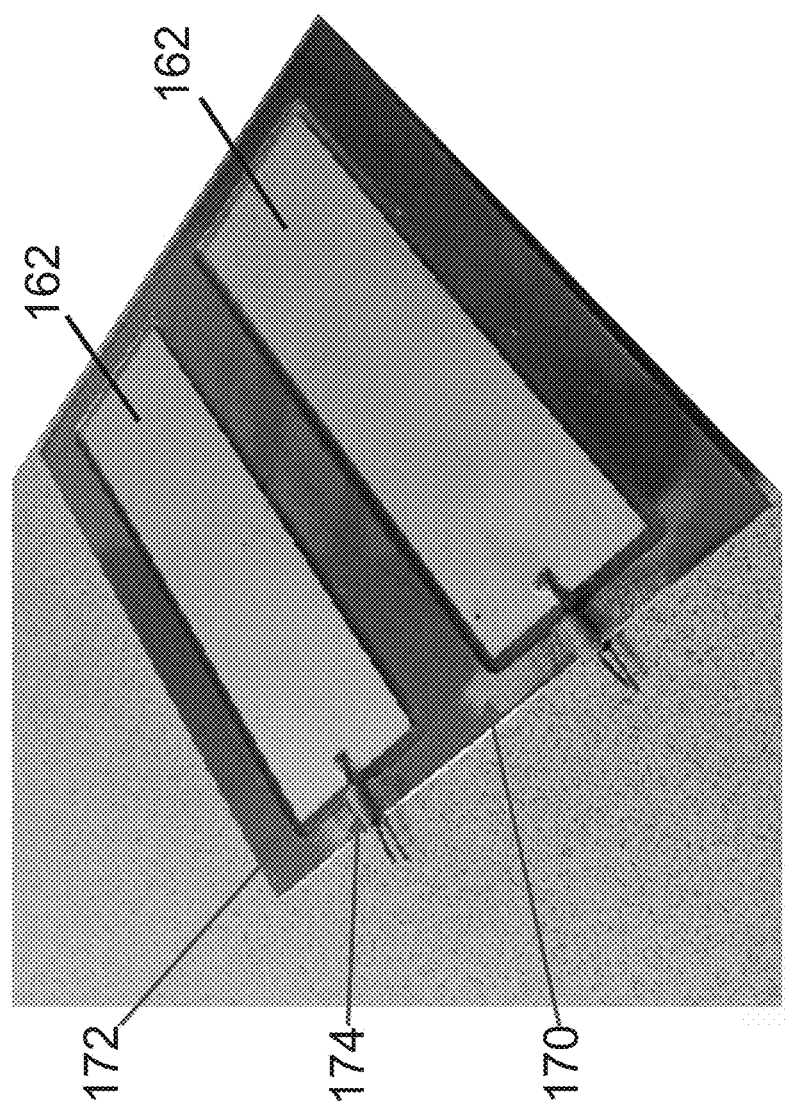
FIG. 5 is a picture showing the holding plate and the piezoelectric element in more detail.

FIG. 5 is a photograph showing the holding plate 170 for the piezoelectric element. Here, the holding plate is made of steel, and provides space for two piezoelectric crystals 162. A silicon potting layer/gasket 172 is located around each piezoelectric crystal, and holds the crystal within the frame provided by the holding plate. Electrical leads 174 are soldered to one end of each crystal as well. With this construction, it is intended that the fluid/particle mixture cannot flow through the holding plate from the first flow chamber to the second flow chamber. Rather, the fluid/particle mixture flows from one end of the acoustic chamber and through one flow chamber, then exit the other end of the acoustic chamber.

It is noted that although the holding plate and the bracket plates are described as separate pieces here, they could be made as one integral piece.

The piezoelectric crystal is usually made of PZT-8 (lead zirconate titanate). Such crystals may have a 1 inch length/width and a nominal 2 MHz resonance frequency. Each piezoelectric element can be formed from only one crystal, or be formed from multiple crystals that each act as a separate ultrasonic transducer and are either controlled by one or multiple amplifiers. This allows each crystal to vibrate in one of its eigenmodes with a high Q-factor. The vibrating crystal is directly exposed to the fluid flowing through the acoustic chamber.

The lack of backing on the piezoelectric crystal(s) (e.g. making the crystal air backed) also permits each piezoelectric crystal to vibrate at higher order modes of vibration with little damping (e.g. higher order modal displacement). The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

Placing the piezoelectric crystals in direct contact with the fluid also contributes to the high Q-factor by avoiding dampening and energy absorption effects. In embodiments, the piezoelectric crystal may be coated to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface.

It is noted that the standing waves generated on the first face and the second face of the piezoelectric element may be different, depending on how the piezoelectric crystals are perturbated by the electrical input. In particular embodiments, the standing waves differ from each other by at least 50 kilohertz (kHz).

Figure 6:
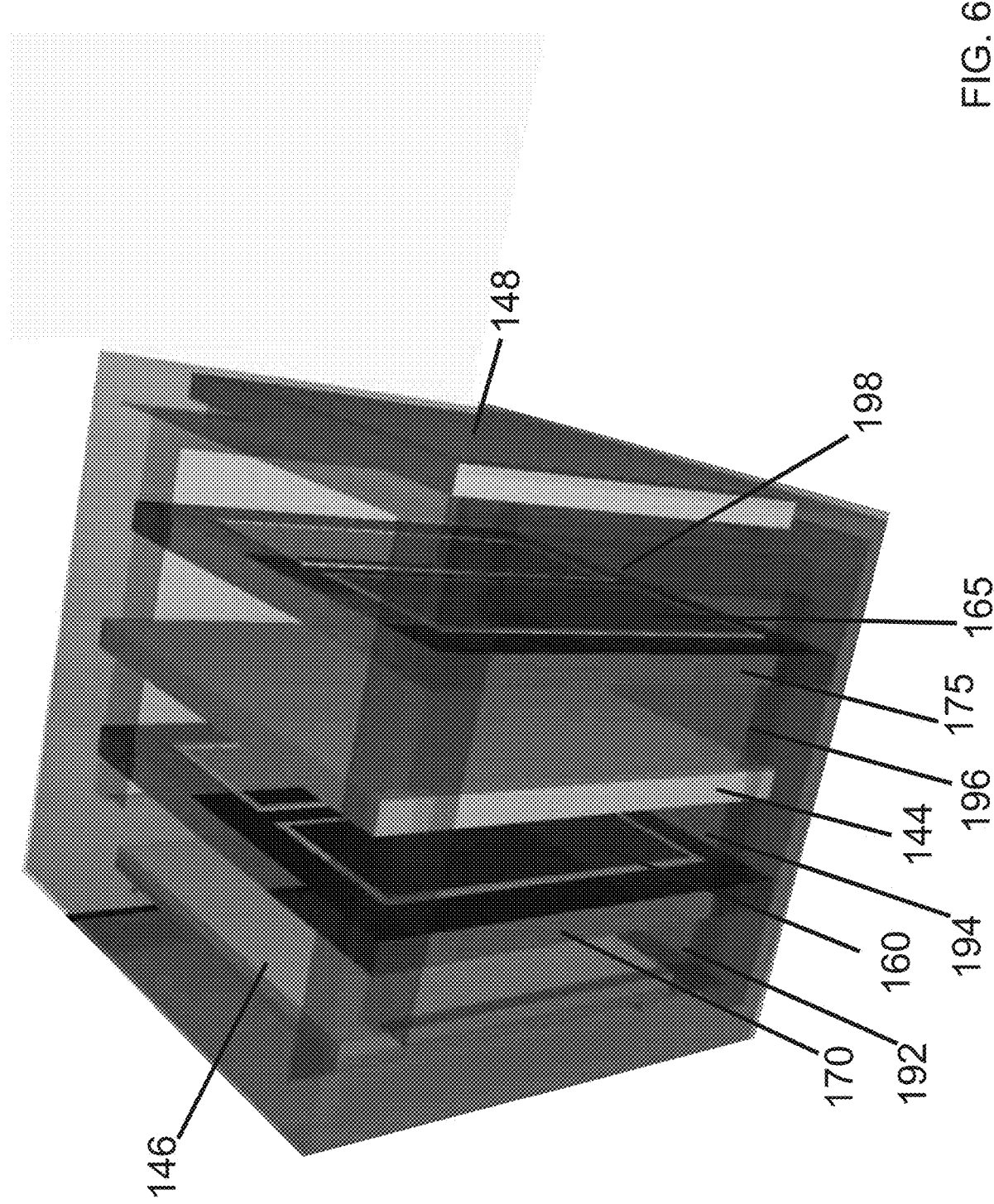
FIG. 6 is a perspective view of a second exemplary embodiment. Here, two piezoelectric elements are placed within the volume of the acoustic chamber. There are a total of three reflectors in the acoustic chamber, two on opposite walls and one in the middle of the acoustic chamber. The acoustic chamber contains four different flow paths through which a fluid/particle mixture can flow.

Generally speaking, the present disclosure relates to the use of the piezoelectric element to generate standing waves on both sides, rather than on only one side as has been done in conventional devices. The present disclosure contemplates that more than one such piezoelectric element can be present within the acoustic chamber. FIG. 6 is a depiction of such an embodiment. In this embodiment, there are two holding plates 170, 175 for two piezoelectric elements 160, 165. There are now three total reflectors in this embodiment. Compared to FIG. 2, the reflector 144 can also be considered a central reflector located between the two piezoelectric elements. The reflector 146 and central reflector 144 are located on opposite sides of the first piezoelectric element 170. The central reflector 144 and third reflector 148 are located on opposite sides of the second piezoelectric element 172. The faces of the reflectors are parallel to the faces of the piezoelectric elements. The central reflector 144 reflects waves generated by both piezoelectric elements 160, 165.

There are now four different flow chambers by which fluid can flow past the piezoelectric elements. A first flow chamber 192 is located between the reflector 146 and the first piezoelectric element 160. A second flow chamber 194 is located between the central reflector 144 and the first piezoelectric element 160. A third flow chamber 196 is located between the central reflector 144 and the second piezoelectric element 165. A fourth flow chamber 198 is located between the reflector 148 and the second piezoelectric element 165. It is noted that in this particular embodiment, the bracket plates 180 would include three slots, two slots for the holding plates 170, 175 and one slot for the central reflector 144.

It is contemplated that any number of piezoelectric elements can be placed within the volume of the acoustic chamber, for example three, four, six, eight, ten, twelve, or even more, as desired by the user. For n piezoelectric elements, there must be (n+1) reflectors in the acoustic chamber, with each piezoelectric element being located between two reflectors. Again, the faces of the piezoelectric element should be parallel to a face of each reflector. The practical number of piezoelectric elements and reflectors is thus constrained by the volume of the acoustic chamber.

Figure 7:
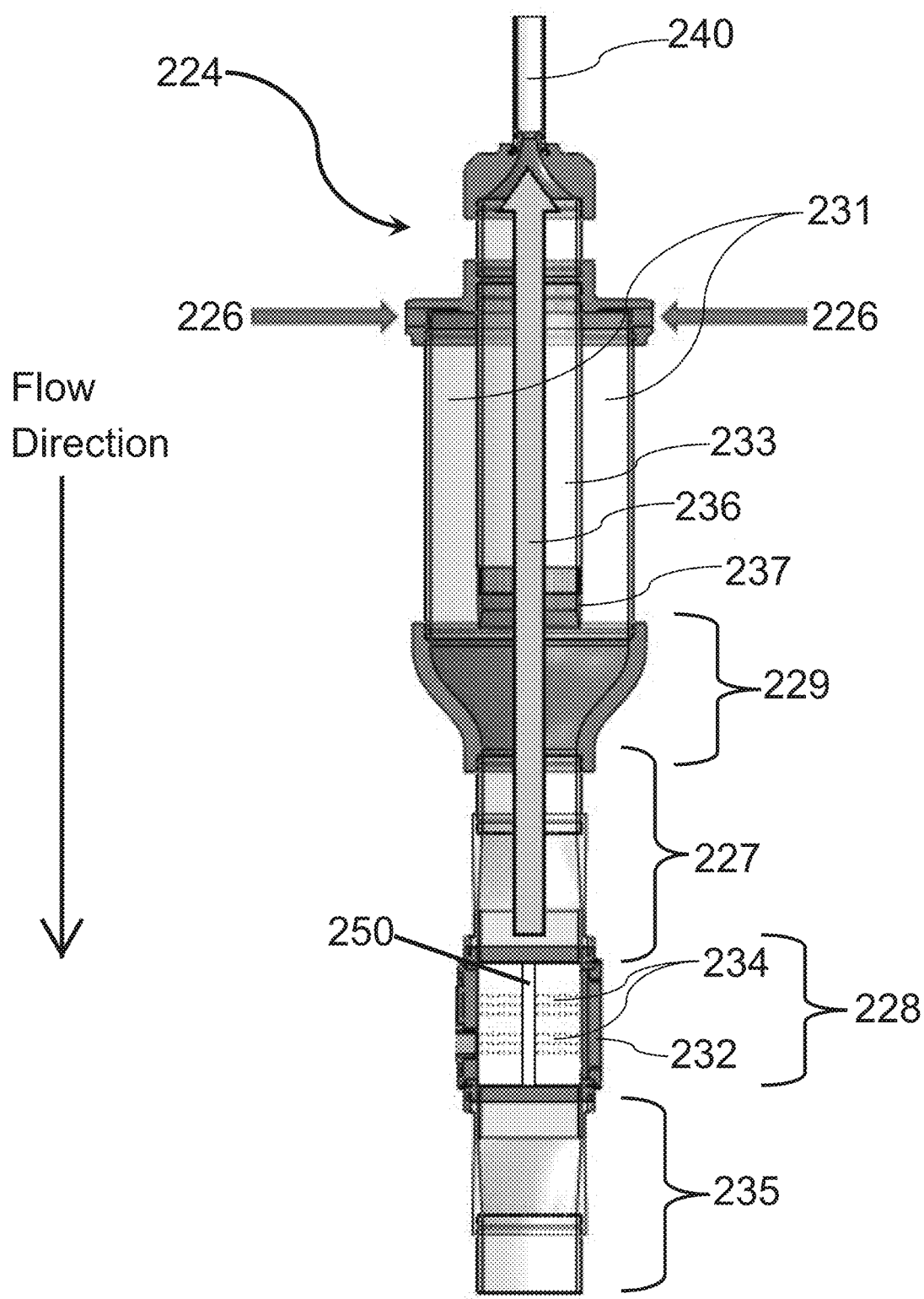
FIG. 7 shows an exemplary acoustophoretic separator for use with the dual acoustophoresis chamber of the present disclosure. Here, fluid flows from the top of the separator through the chamber and out the bottom of the separator.
Figure 8:
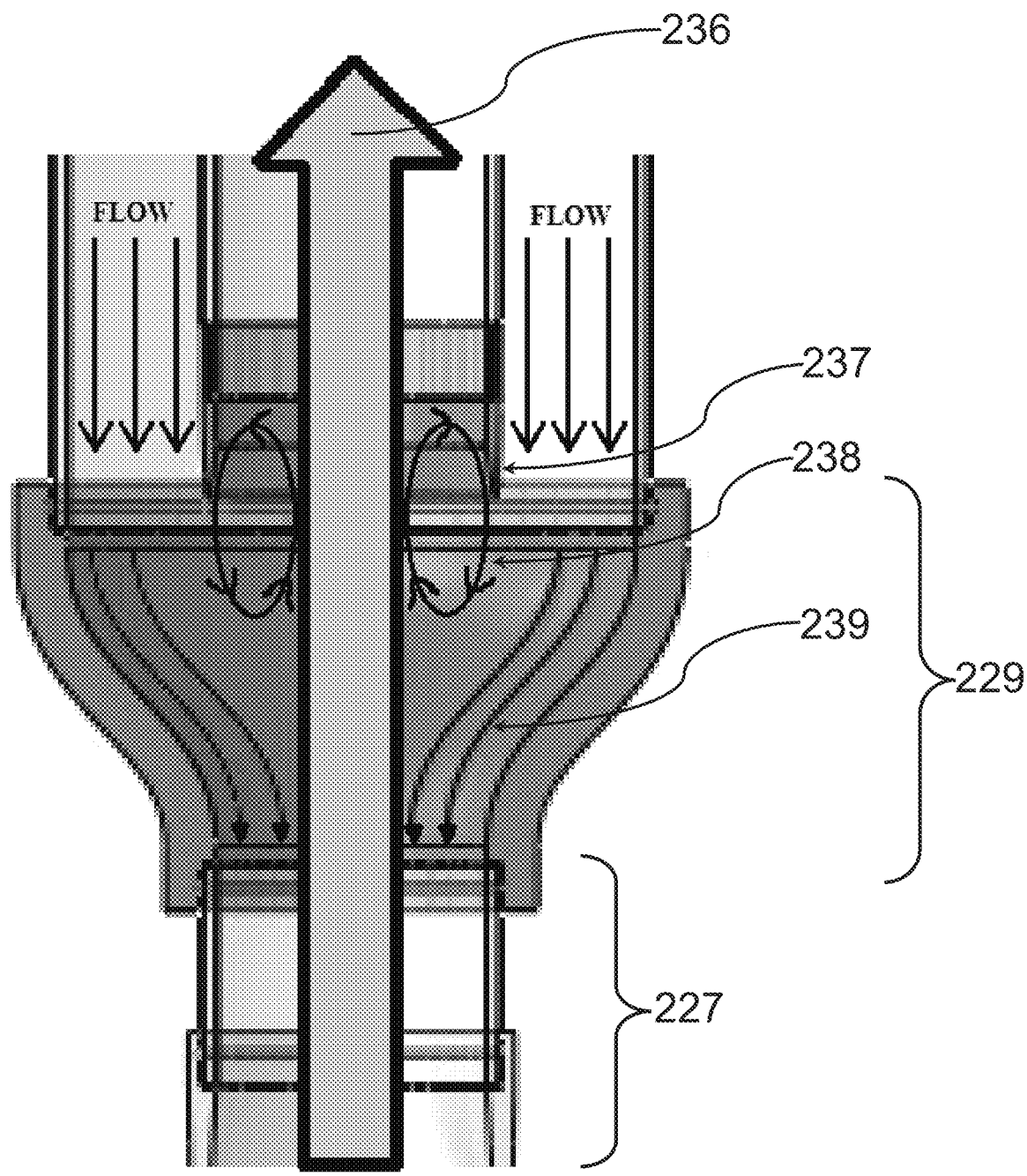
FIG. 8 is a magnified view of fluid flow near the intersection of the contoured nozzle wall and the collection duct in the separator of FIG. 7.

FIG. 7 and FIG. 8 are side views of one type of acoustophoretic device in which the dual acoustophoresis chamber can be used. The device is shown here in an orientation where the flow direction is downwards, which is used for separating less-dense particles from the host fluid. However, the device may be essentially turned upside down to allow separation of particles which are heavier than the host fluid (similar to FIG. 1). Instead of a buoyant force in an upward direction, the weight of the agglomerated particles due to gravity pulls them downward. It should be noted that this embodiment is depicted as having an orientation in which fluid flows vertically. However, it is also contemplated that fluid flow may be in a horizontal direction, or at an angle.

A particle-containing fluid flows into the device through inlets 226 into an annular plenum 231. The annular plenum has an annular inner diameter and an annular outer diameter. Two inlets are visible in this illustration, though it is contemplated that any number of inlets may be provided as desired. In particular embodiments, four inlets are used. The inlets are radially opposed and oriented.

A contoured nozzle wall 229 reduces the outer diameter of the flow path in a manner that generates higher velocities near the wall region and reduces turbulence, producing near plug flow as the fluid velocity profile develops, i.e. the fluid is accelerated downward in the direction of the centerline with little to no circumferential motion component and low flow turbulence. This generates a chamber flow profile that is optimum for acoustic separation and particle collection. The fluid passes through connecting duct 227 and into the acoustic chamber 228.

As seen in the zoomed-in contoured nozzle 229 in FIG. 8, the nozzle wall also adds a radial motion component to the suspended particles, moving the particles closer to the centerline of the apparatus and generating more collisions with rising, buoyant agglomerated particles. This radial motion will allow for optimum scrubbing of the particles from the fluid in the connecting duct 227 prior to reaching the separation chamber. The contoured nozzle wall 229 directs the fluid in a manner that generates large scale vortices at the entrance of the collection duct 233 to also enhance particle collection. Generally, the flow area of the device 224 is designed to be continually decreasing from the annular plenum 231 to the acoustic chamber 228 to assure low turbulence and eddy formation for better particle separation, agglomeration, and collection. The nozzle wall has a wide end and a narrow end. The term scrubbing is used to describe the process of particle/droplet agglomeration, aggregation, clumping or coalescing, that occurs when a larger particle/droplet travels in a direction opposite to the fluid flow and collides with smaller particles, in effect scrubbing the smaller particles out of the suspension.

Returning to FIG. 7, the acoustic chamber 228 includes reflectors 232 on opposite sides of the chamber, and a piezoelectric element within the chamber. In use, standing waves 234 are created between the piezoelectric element and each reflector 232. These standing waves can be used to agglomerate particles, and this orientation is used to agglomerate particles that are buoyant (e.g. oil). The fluid/particle mixture flows through both flow chambers in the same direction, i.e. in parallel. Fluid, containing residual particles, then exits or egresses the device through outlet 235.

As the buoyant particles agglomerate, they eventually overcome the combined effect of the fluid flow drag forces and acoustic radiation force, and their buoyant force 236 is sufficient to cause the buoyant particles to rise upwards. In this regard, a collection duct 233 is surrounded by the annular plenum 231. The larger particles will pass through this duct and into a collection chamber 240. This collection chamber can also be part of an outlet duct. The collection duct and the flow outlet are on opposite ends of the device.

It should be noted that the buoyant particles formed in the separation chamber 228 subsequently pass through the connecting duct 227 and the nozzle wall 229. This causes the incoming flow from the annular plenum to flow over the rising agglomerated particles due to the inward radial motion imparted by the nozzle wall. This allows the rising particles to also trap smaller particles in the incoming flow, increasing scrubbing effectiveness. The length of the connecting duct 227 and the contoured nozzle wall 229 thus increase scrubbing effectiveness. Especially high effectiveness is found for particles with a size of 0.1 microns to 20 microns, where efficiency is very low for conventional methods.

The device of FIG. 7 is shaped such that fluid flows into the device through the device inlet, into the first end of the acoustic chamber, then flows in parallel through the first flow chamber and the second flow chamber, out of the acoustic chamber through the second end of the acoustic chamber, and out of the device through the device outlet. This design provides an optimized velocity profile with low flow turbulence at the inlet to the acoustic chamber 228, a scrubbing length before the flow chamber to enhance particle agglomeration and/or coalescence before acoustic separation, and the use of the collection vortices to aid particle removal at the collection duct 233.

Figure 9:
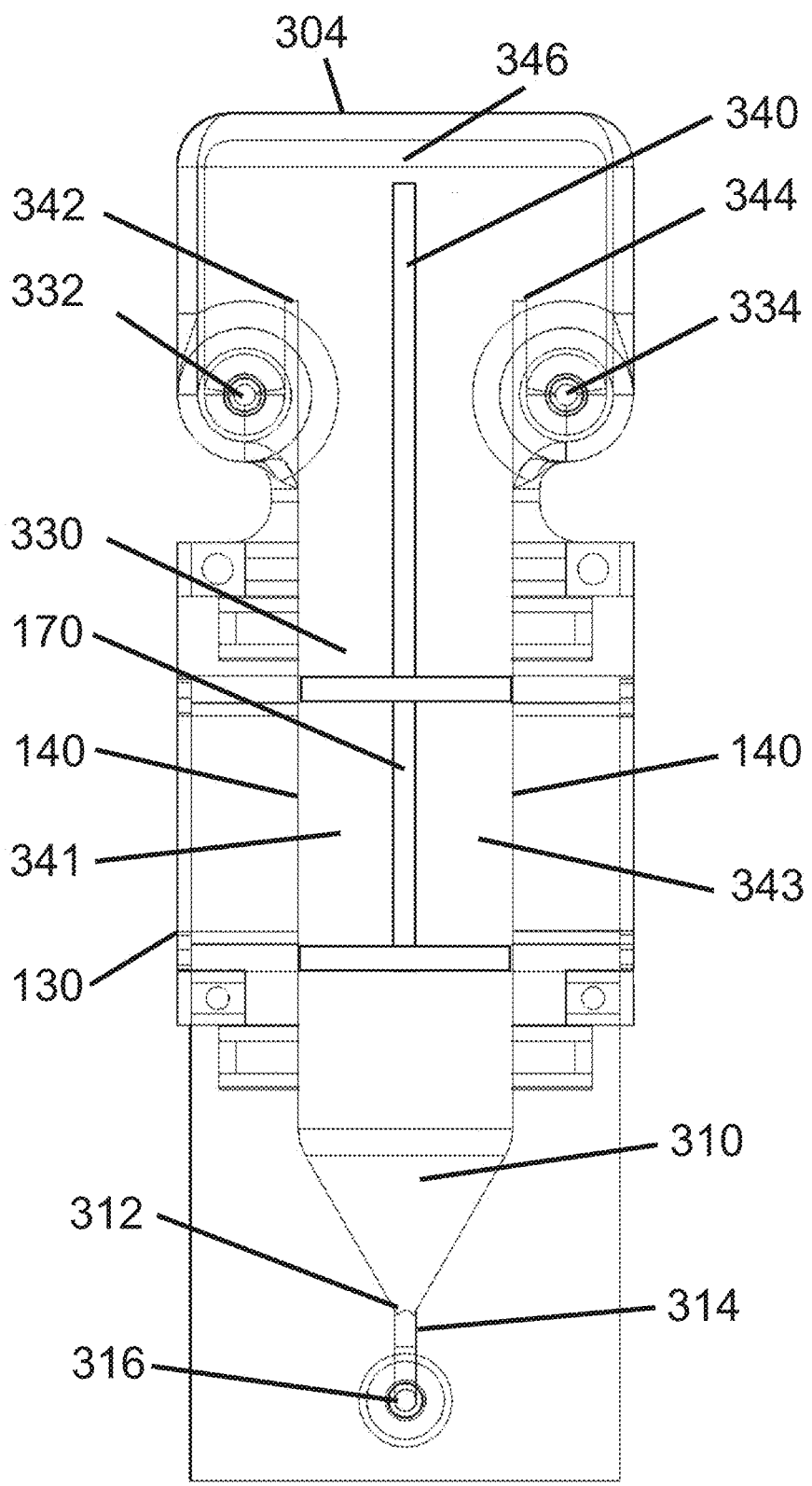
FIG. 9 is a front view of a second exemplary acoustophoretic device in which fluid flows in through an inlet at the top of the device, and then travels in a U-shaped flow path through the acoustophoretic chamber and then exits through an outlet at the top of the device as well. Separated particles are collected through a well at the bottom of the device.

An alternative device design that can incorporate the dual acoustophoresis chamber is shown in FIG. 9. In this device, the inlet and outlet are both located at the same end of the device (here, the upper end). A fluid/particle mixture is pumped in through the inlet port 332. The mixture flows downwards via gravity through the acoustic chamber, where the particles are trapped and held by the ultrasonic standing wave. As fluid continues to be pumped into the flow path, eventually the device is filled with fluid, and the fluid pressure rises high enough that fluid will flow out through the outlet 334 at the top of the device. The particles within the ultrasonic standing waves collect or agglomerate, and eventually grow to a size where gravity overcomes the acoustic force of the standing wave, and the particle aggregates then fall/sink into a collection well 310 that tapers downwards in cross-sectional size to a vertex 312. A drain line 314 connects the vertex 312 to a port 316 where the concentrated particles can be drawn out of the well.

As illustrated here, a wall 340 is located in the flow channel 330 between the inlet 332 and the outlet 334. Fluid thus flows from the inlet downwards through the acoustic chamber through the first flow chamber, then back upwards through the second flow chamber and then to the outlet. The cross-sectional area of the first flow chamber can be smaller than, equal to, or greater than the cross-sectional area of the second flow chamber. As illustrated here, the wall (of which the holding plate is a part) is placed so that the cross-sectional area 341 of the flow channel for the inlet port is smaller than the cross-sectional area 343 of the flow channel for the outlet port.

Also visible is a first retainer wall 342 adjacent the inlet and a second retainer wall 344 adjacent the outlet. As seen here, the inlet 332 and the outlet 334 are located relatively close to the middle of the front wall, and are spaced apart from the upper end 304 of the device. Incoming fluid must flow towards the upper end 304 and then over the first retainer wall 342 before flowing into the acoustic chamber. Similarly, fluid coming back from the acoustic chamber must flow over the second retainer wall 344 before exiting through the outlet 334. This construction provides a means by which the turbulence of incoming fluid can be reduced, so that the particles trapped in the acoustic standing wave in the acoustic chamber are not disrupted or washed out of the standing wave before aggregating to a sufficient size.

As also depicted here, in some embodiments, the wall 340 is spaced apart from the upper end 304 of the housing. This gap 346 forms and acts as a pressure relief passage between the inlet 332 and the outlet 334, for example in case the flow path is inadvertently blocked.

As a result of this construction, fluid flows into the device through the device inlet, then travels through the acoustic chamber in a U-shaped path from the first end of the acoustic chamber to the second end through the first flow chamber and then back to the first end through the second flow chamber, then exits the flow chamber through the first end of the acoustic chamber and exits the device through the device outlet.

The various components of the acoustic chamber containing the piezoelectric element can be made of any appropriate material, such as polycarbonate, acrylic (e.g. polymethyl methacrylate), or glass (e.g. soda lime or borosilicate), or polypropylene. It is generally desirable for the material to be somewhat transparent, so that a clear window can be produced and the internal flow channels and flow paths can be seen during operation of the acoustophoresis device/system.

Various coatings may be used on the internal flow channels of the modules. Such coatings include epoxies, for example epichlorohydrin bisphenol-A crosslinked with an amine or a polyamide; or polyurethane coatings, for example a polyester polyol crosslinked with aliphatic isocyanates, or a silicone coating or a polyoxyalkylene coating.

Such coatings are useful for producing a smooth surface and/or reducing surface tension, permitting cells to slide better under the influence of gravity along the flow channel surface and into desired locations (such as the collection well).

The flow rate of the acoustophoretic device must be controlled so that gravity can act on particle aggregates. In this regard, it is contemplated that the particle/fluid mixture passing in/out of the flow path in the acoustophoretic device can flow at rates of up to about 100 milliliters per minute (ml/min).

In the present systems, the system is operated at a voltage such that the particles are trapped in the ultrasonic standing waves, i.e., remain in a stationary position. The particles are collected in along well defined trapping lines, separated by half a wavelength. Within each nodal plane, the particles are trapped in the minima of the acoustic radiation potential. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particle. The radial or lateral component of the acoustic radiation force is on the same order of magnitude as the axial component of the acoustic radiation force. As discussed above, the lateral force can be increased by driving the piezoelectric element in higher order mode shapes, as opposed to a form of vibration where the piezoelectric element effectively moves as a piston having a uniform displacement. The acoustic pressure is proportional to the driving voltage. The electrical power is proportional to the square of the voltage.

In embodiments, the pulsed voltage signal driving the piezoelectric element can have a sinusoidal, square, sawtooth, or triangle waveform; and have a frequency of 500 kHz to 10 MHz. The pulsed voltage signal can be driven with pulse width modulation, which produces any desired waveform. The pulsed voltage signal can also have amplitude or frequency modulation start/stop capability to eliminate streaming.

The size, shape, and thickness of the piezoelectric crystal determines the displacement at different frequencies of excitation, which in turn affects separation efficiency. Typically, the piezoelectric element is operated at frequencies near the thickness resonance frequency (half wavelength). Gradients in displacement typically result in more places for particles to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the piezoelectric element.

Figure 10:
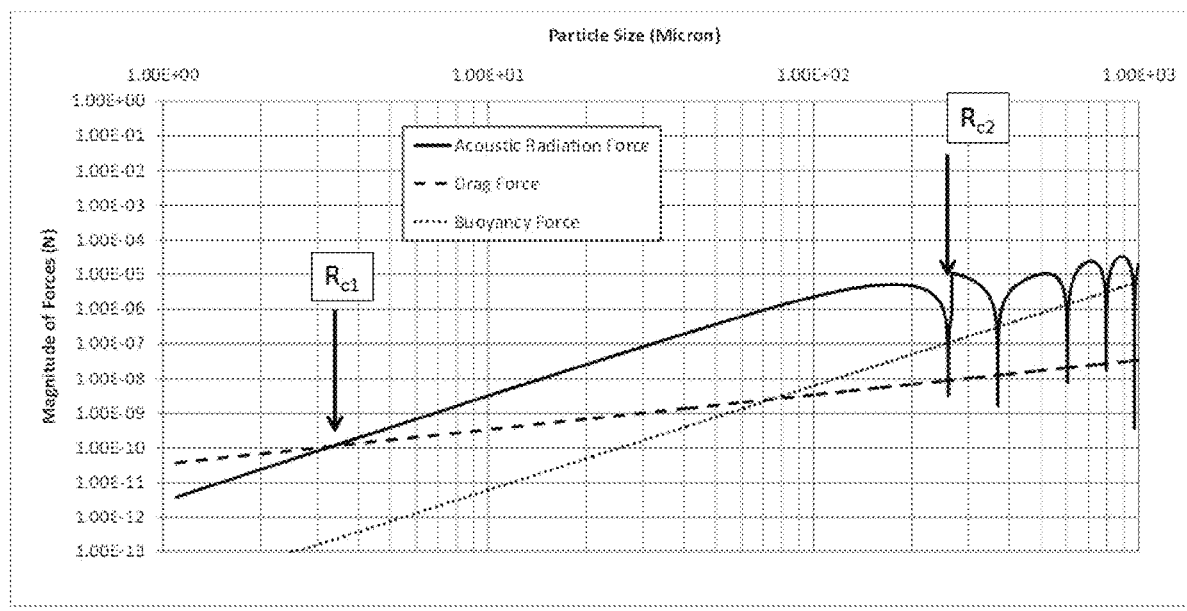
FIG. 10 is a graph showing the relationship of the acoustic radiation force, buoyancy force, and Stokes' drag force to particle size. The horizontal axis is in microns (μm) and the vertical axis is in Newtons (N).

FIG. 10 is a lin-log graph (linear y-axis, logarithmic x-axis) that shows the scaling of the acoustic radiation force, fluid drag force, and buoyancy force with particle radius. Calculations are done for a typical SAE-30 oil droplet used in experiments. The buoyancy force is a particle volume dependent force, and is therefore negligible for particle sizes on the order of micron, but grows, and becomes significant for particle sizes on the order of hundreds of microns. The fluid drag force scales linearly with fluid velocity, and therefore typically exceeds the buoyancy force for micron sized particles, but is negligible for larger sized particles on the order of hundreds of microns. The acoustic radiation force scaling acts differently. When the particle size is small, the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 10 this happens for a particle size of about 3.5 micron, labeled as Rd. The graph then indicates that all larger particles will be trapped as well. Therefore, when small particles are trapped in the standing wave, particles coalescence/clumping/aggregation/agglomeration takes place, resulting in continuous growth of effective particle size. As the particle size grows, the acoustic radiation force reflects off the particle, such that large particles will cause the acoustic radiation force to decrease. Particle size growth continues until the buoyancy force becomes dominant, which is indicated by a second critical particle size, $R_{c2}$, at which size the particles will rise or sink, depending on their relative density with respect to the host fluid. As the particles rise or sink, they no longer reflect the acoustic radiation force, so that the acoustic radiation force then increases. Not all particles will drop out, and those remaining particles will continue to grow in size as well. This phenomenon explains the quick drops and rises in the acoustic radiation force beyond size $R_{c2}$. Thus, FIG. 10 explains how small particles can be trapped continuously in a standing wave, grow into larger particles or clumps, and then eventually will rise or settle out because of increased buoyancy force.

The following examples are for purposes of further illustrating the present disclosure. The examples are merely illustrative and are not intended to limit devices made in accordance with the disclosure to the materials, conditions, or process parameters set forth therein.

Examples

A conventional acoustophoresis device was used as a Comparative Example. This device used an acoustic chamber in which the ultrasonic transducer was located on one wall of the chamber, and a reflector was located on the opposite wall. The transducer had one piezoelectric crystal of dimensions 1 inch×3 inches.

An acoustophoresis device of the present disclosure is labeled as Example. This device used an acoustic chamber in which the piezoelectric crystal was mounted in the middle of the acoustic chamber. Two reflectors were located on opposite walls, parallel to the face of the one piezoelectric crystal. This piezoelectric crystal also had dimensions 1 inch×3 inches.

Figure 11:
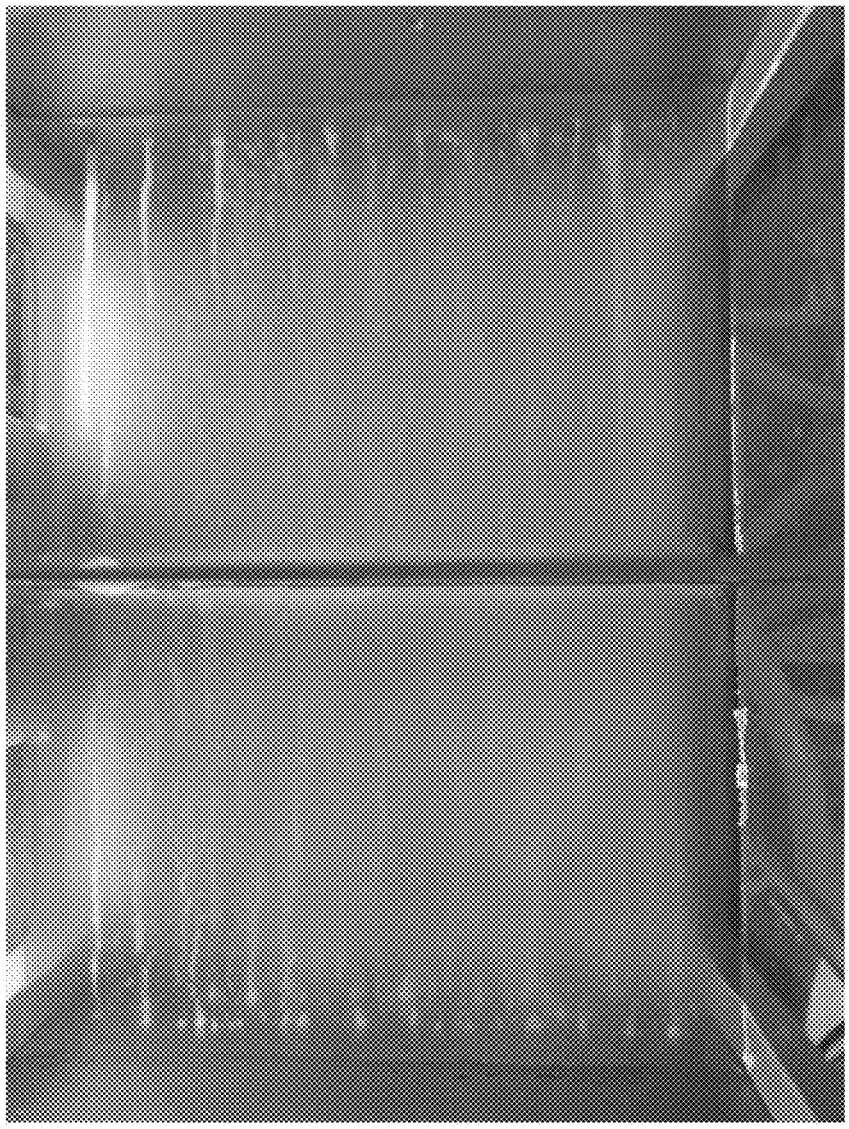
FIG. 11 is a picture showing the dual acoustophoresis chamber of the present disclosure being operated. The trapping lines are visible.

The two devices were then operated with a yeast slurry as the feed input. The slurry contained 0.5% solids. The devices were operated over 40 minutes of operation. FIG. 11 is a picture illustrating operation of the dual acoustophoresis chamber. The trapping lines generated by the piezoelectric element located in the middle of the chamber are visible.

Samples were periodically taken from the acoustic chamber. After 40 minutes of operation, the concentrate, permeate, and retentate were measured as well. The concentrate was the portion exiting the device that contained the concentrated yeast, along with some fluid. The permeate was the filtered portion exiting the device, which was mostly liquid with a much lower concentration of yeast. The retentate was the remaining substance left in the device after operation. The results are provided in the following table.

|  | Comparative Example | Example |
|---|---|---|
| Feed Turbidity (NTU) | 876 | 978 |
| Retentate Turbidity (NTU) | 1345 | 1708 |
| Concentrate Turbidity (NTU) | 3620 | 2164 |
| Permeate Turbidity (NTU) | 71.6 | 88.1 |
| Overall Efficiency (%) | 92 | 91 |

As seen from these results, the efficiency of the dual acoustophoretic chamber, wherein the piezoelectric element is located within the volume of the chamber and divides the chamber into multiple flow chambers, is about equal to that of the conventional system illustrated by the Comparative Example.

Figure 12:
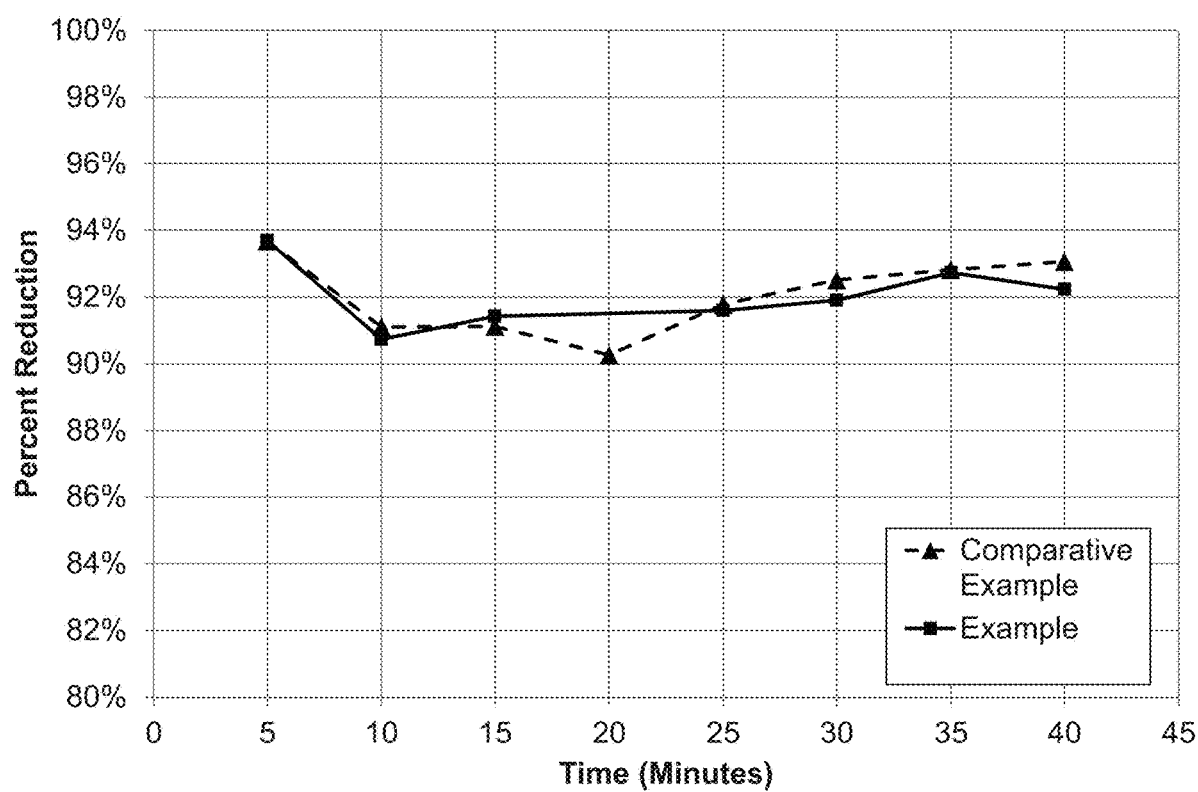
FIG. 12 is a graph showing device efficiency over time, showing equivalent operation over time for both the conventional system and the dual acoustophoresis chamber of the present disclosure.

FIG. 12 is a chart showing the efficiency in terms of percent reduction in turbidity from the feed, over time. As seen here, the present device is just as efficient and effective over time as the conventional system.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An acoustophoresis device, comprising:
an acoustic chamber with a fluid path between a first end and a second end different from the first end;
an ultrasonic transducer in the acoustic chamber and aligned with the fluid path such that fluid can flow along two sides of the ultrasonic transducer, such that the ultrasonic transducer is fluid backed, the ultrasonic transducer comprising a piezoelectric element;
wherein the ultrasonic transducer is configured to be excited such that the piezoelectric element vibrates in a higher order mode to generate an acoustic wave on each of the two sides of the ultrasonic transducer to trap and agglomerate particles in the fluid into larger particles that grow to a point where they exit the acoustic wave.

2. The acoustophoresis device of claim 1, further comprising at least two reflectors, each reflector being opposed to one of the two sides of the ultrasonic transducer.

3. The acoustophoresis device of claim 1, wherein the ultrasonic transducer further comprises first and second piezoelectric elements aligned with and opposed to each other.

4. The acoustophoresis device of claim 3, wherein the first and second piezoelectric elements are configured to be excited at the same frequency as, or a different frequency from each other.

5. The acoustophoresis device of claim 1, wherein the ultrasonic transducer divides the acoustic chamber into equal or unequal portions.

6. The acoustophoresis device of claim 1, further comprising a contoured nozzle wall between a device inlet and the acoustic chamber.

7. The acoustophoresis device of claim 1, wherein the fluid path is configured to permit fluid flow through the acoustic chamber in a U-shaped path from a device inlet to a device outlet.

8. The acoustophoresis device of claim 7, further comprising:
a well that tapers downwards in cross-sectional area from a single inlet to a vertex, and that communicates with the second end of the acoustic chamber; and
a drain line connecting the vertex to a port for recovering material collected in the well.

9. The acoustophoresis device of claim 1, further comprising another ultrasonic transducer in the acoustic chamber and aligned with the fluid path such that fluid can flow along two sides of the another ultrasonic transducer, the another ultrasonic transducer comprising another piezoelectric element.

10. The acoustophoresis device of claim 1 wherein:
the ultrasonic transducer includes a first face and a second face that are each directly exposed to the fluid path; or
one or more of the first face or the second face of the ultrasonic transducers include a wear layer; or
the ultrasonic transducer is made up of at least two piezoelectric elements, a first piezoelectric element forming the first face and a second piezoelectric element forming the second face.

11. The acoustophoresis device of claim 3, wherein the first piezoelectric element is configured to be operated at the same higher order mode as, or a different higher order mode from, the second piezoelectric element.

* * * * *